(12) United States Patent
Longo

(10) Patent No.: US 11,208,444 B2
(45) Date of Patent: Dec. 28, 2021

(54) BRCA2-MEDIATED PURIFICATION OF RECOMBINASE PROTEIN

(71) Applicant: Idea Seed, LLC, City of Industry, CA (US)

(72) Inventor: Michael Longo, Whittier, CA (US)

(73) Assignee: Idea Seed, LLC., City of Industry, CA (US)

(*) Notice: Subject to any disclaimer, the term of this patent is extended or adjusted under 35 U.S.C. 154(b) by 0 days.

(21) Appl. No.: 16/804,702

(22) Filed: Feb. 28, 2020

(65) Prior Publication Data

US 2020/0291080 A1   Sep. 17, 2020

Related U.S. Application Data

(63) Continuation-in-part of application No. 15/555,966, filed as application No. PCT/US2016/021282 on Mar. 7, 2016, now Pat. No. 10,604,778.

(60) Provisional application No. 62/128,512, filed on Mar. 5, 2015.

(51) Int. Cl.
   *C07K 14/47*       (2006.01)

(52) U.S. Cl.
   CPC .......... *C07K 14/47* (2013.01); *C07K 2319/21* (2013.01); *C07K 2319/24* (2013.01)

(58) Field of Classification Search
   None
   See application file for complete search history.

(56) References Cited

U.S. PATENT DOCUMENTS

| 2006/0234293 A1* | 10/2006 | Venkitaraman .... C07K 14/4702 435/7.1 |
| 2008/0280327 A1* | 11/2008 | Larsen ..................... A61P 1/04 435/69.7 |
| 2013/0203116 A1* | 8/2013 | Kowalczykowski .. C12N 15/62 435/69.7 |

OTHER PUBLICATIONS

Nomme et al. J. Med. Chem. 2010, 53, 5782-5791 (Year: 2010).*
Scott et al. FEBS Lett. Apr. 2016; 590(8): 1094-1102. (Year: 2016).*
Chica et al. Curr Opin Biotechnol. Aug. 2005;16(4):378-84. (Year: 2005).*
Singh et al. Curr Protein Pept Sci. 2017, 18, 1-11 (Year: 2017).*

* cited by examiner

*Primary Examiner* — Christian L Fronda
(74) *Attorney, Agent, or Firm* — Marshall A. Lerner; Brad Mattes; Kleinberg & Lerner, LLP

(57) ABSTRACT

The invention is the products and methods associated with purifying overexpressed recombinant recombinases from a host cell line resulting in an un-tagged protein of interest without any additional, non-native amino acids. The invention employs at least one DNA vector that co-expresses a tagged fusion protein and the recombinase protein with the recombinase protein having an affinity for binding to the tagged fusion protein. Isolation methods of the recombinase protein include the targeting of the tagged fusion protein.

14 Claims, 16 Drawing Sheets

Specification includes a Sequence Listing.

BRCA2-MEDIATED PURIFICATION OF RECOMBINASE PROTEIN

This application is a continuation-in-part of U.S. Non-Provisional application Ser. No. 15/555,966 filed Sep. 5, 2017, which is a national stage application of PCT/US16/21282 filed Mar. 7, 2016, which claims the benefit of priority to U.S. Provisional Application No. 62/128,512 filed Mar. 5, 2015.

BACKGROUND OF THE INVENTION

1. Field of the Invention

The present invention relates to methods for isolation of recombinant proteins, and namely methods that involve the purification of recombinases.

2. General Background and State of the Art

Recombinases play a vital role in the life cycle of a cell. In Prokaryotes, the RecA recombinase is the molecular machine that facilitates repair of DNA double strand breaks (DSBs) via homologous recombination. In Eukaryotes, Rad51 and Dmc1 are the RecA homologs that mediate homologous recombination.

Both RAD51 and DMC1 proteins coded for by the Rad51 and Dmc1 genes, respectively, have a molecular weight of roughly 37 kilodaltons (kDa), have very similar amino acids sequences, and unsurprisingly are structural homologs as well. The common features of these recombinases are 1) a conserved globular ATPase domain joined by 2) an elbow-like linker region to a 3) pendulum-like bundle of helices in the N-terminus of the structure. The ATPase domain binds and hydrolyzes ATP through conserved Walker A and Walker B motifs, but also contains flexible loops, L1 and L2, which are responsible for the DNA binding capacity of the proteins. The role of the N-terminal domain is thought to also involve DNA interaction in some capacity.

Within the elbow-like linker region, which physically connects these two domains, is a conserved F-X-X-A motif in humans, with F representing phenylalanine, X representing a non-conserved molecule, including synthetic, non-proteinogenic, and post-translationally modified amino acids, and A representing alanine. Alanine is not 100% conserved, and some archeal RadA proteins, such as Methanococcus voltae RadA (SEQ ID 27), contain a glycine (G) in the place of alanine (A) creating an F-X-X-G motif. Scott et. al., FEBS Lett., 590(8): 1094-1102 (2016); Wu et. al. Mol. Cell. 15(3); 423-425 (2004).

It is through this motif that these recombinases are able to polymerize into higher order multimeric structures. The larger hydrophobic residue, F, plugs into a deep hydrophobic pocket located in the globular ATPase domain of a neighboring molecule, while the A residue sits in an adjacent shallower pocket. This sort of head-to-tail arrangement facilitates the formation of large macromolecular structures, like the nucleoprotein filaments that both RAD51 and DMC1 have been shown to produce.

An important interaction of RAD51 is with the Breast Cancer Susceptibility Protein 2, BRCA2. BRCA2 interacts with RAD51 through 2 separate and distinct modes. One mode is characterized by the interaction of RAD51 with the BRC repeat region of BRCA2, which in humans consist of 8 BRC repeats termed BRC1-8. The BRC repeat binds mainly by mimicking RAD51 multimeric association. Thus, the BRC repeat contains a conserved F-X-X-A motif and binds to the pockets of a RAD51 ATPase domain. In addition to the conserved F-X-X-A motif, BRC repeats make additional contacts with the RAD51 ATPase domain further stabilizing the interaction. In this mode of binding, one RAD51 molecule binds to one BRC repeat in a 1:1 ratio.

As is the case for RAD51 and DMC1, alanine is not 100% conserved in the F-X-X-A BRC motif. For example, *Arabidopsis* and *Ustilago* homologous proteins, SEQ ID 28 and SEQ ID 29, respectively, contain a glycine (G) in the place of alanine (A), creating an F-X-X-G motif. Siaud et. al., EMBO J. 23:1392-1401 (2004).

In organisms that do not have the BRCA2 gene or a BRC repeat equivalent, that organism's RAD51 homolog can be mutated to bind to a BRC repeat. Shin et. al., EMBO J., 22(17): 4566-4576 (2003).

Although the F-X-X-A motif is generally conserved in BRC repeats, recent studies have demonstrated the F-X-X-A motif can be mutated and maintain binding interation with RAD51. For example, Phenylalanine (F) mutated to tryptophan (W) has been demonstrated to increase binding affinity. Scott et. al., FEBS Lett., 590(8): 1094-1102 (2016). When the terminal alanine is mutated to serine (S), the resulting motif exhibits increased binding interactions. Nomme et. al., J. Med. Chem., 53(15): 5782-5791 (2010).

The F-X-X-A motif has also been demonstrated to maintain binding interactions with RAD51 when mutated to include non-proteinogenic amino acids. Recent developments enable the synthesis of peptides composed of non-proteinogenic and synthetic amino acids. Hartman et. al., PLoS ONE, 2(10): e972 (2007); Fan et. al., Biochim Biophys Acta. 1861(11 Pt B): 3024-3029 (2017). For example, the terminal alanine of the F-X-X-A motif can be mutated to α-amino butyric acid (U). Scott et. al., FEBS Lett., 590(8): 1094-1102 (2016).

In the C-terminal region of BRCA2 is another motif that binds to RAD51, but through a different molecular approach, as it binds to a multimeric form of RAD51, as opposed to the 1:1 stoichiometry of the BRC interaction.

Upon the occurrence of a DSB, the broken DNA ends are resected by the Exo1/Dna2 nucleases to yield 3' single stranded overhangs. RAD51 monomers bind and polymerize along the length of the 3' overhangs, producing RAD51 nucleoprotein filaments. It is the RAD51 nucleoprotein filament that drives the subsequent search for homologous sequence.

This search for a homologous sequence is accomplished specifically by catalyzing the invasion of the 3' overhang strand into an intact double strand DNA molecule, typically a sister chromosome. This process is termed strand invasion. The invading 3' overhang can base pair with the homologous sequence and use the complementary sequence as a template to initiate repair synthesis.

The DMC1 recombinase performs the same role as RAD51, but in meiotic cells where DSBs are intentionally introduced during meiosis. The ensuing strand invasion is critical for the pairing of homologous chromosomes during prophase 1.

Standard established protocols for the purification of recombinant Rad51 and Dmc1 have typically involved a spermadine precipitation step as an initial means of isolating the target protein from soluble lysate, followed by subsequent resolubilizing and further chromatographic separation. The yields of such protocols are not abundant and as a consequence, frequent re-preparation is required.

Alternatively, to the precipitation-based method, purification of RAD51/DMC1 has also been accomplished by fusing an affinity tag to either the amino-terminus or the carboxy-terminus of the target protein. Though such tags can be engineered to be proteolytically removed, such a process generally leaves additional residues not present in the native protein sequence. In addition, the requirement for a sequence-specific protease can be burdensome and incur additional cost.

INVENTION SUMMARY

The invention is the products and methods associated with purifying overexpressed recombinant RAD51 or DMC1 proteins by utilizing their natural protein-protein interactions to efficiently isolate and enrich them from the soluble lysate, then subsequently separate them from their cognate interaction partner in a later chromatographic step. The final product is the full length, un-tagged protein of interest without any additional, non-native amino acids.

Recombinant RAD51 or DMC1 protein expression can be done in any expression system of choice (i.e. bacteria, yeast, insect cell, or mammalian cell).

Possible bacterial strains that may be used for the cloning and expression of the recombinant vector may be, but not limited to D5a, BL21, BL21 (DE3), JM109, JM109 (DE3), HB101 or derivatives thereof. Possible plasmids for gene modification and protein expression in said bacteria may be any of the pET vectors as described in the Novagen pET System Manual (www.emdmillipore.com) or any pBAD expression vectors provided by Invitorgen Life Technologies (www.lifetechnologies.com). pQE vectors may also be used to create a recombinant vector. In another preferred embodiment, a pRSF-Duet 1 dual expression vector (Novagen) may also be used.

In the alternate, the RAD51 or DMC1 containing construct may also be expressed in a mammalian cell system. Possible plasmids for use in mammalian cellular expression systems may be a pcDNA expression vector under the control of a CMV promoter such as pcDNA3.1+ as provided by Life Technologies (www.lifetechnologies.com) or a high expression vector such pEF-BOS or a pEF-BOS derivative as described by Mizushima et. al. Nuc. Adi. Res. 18:17 (1990). Possible mammalian cell lines may be HEK293E suspension cells.

The recombinant RAD51 protein is co-overexpressed with a fusion protein wherein the fusion protein includes sequences for an affinity tag (such as MBP or GST), and the BRC4 F-X-X-A repeat motif of the Breast Cancer Susceptibility Protein (BRCA2). An additional tag such as a polyhistidine tag (hisTag) generally of six histidine residues may be added to the fusion protein to facilitate another affinity tag that may be utilized for recombinant protein purification. The sequence for the RAD51 protein can be the full-length, native sequence or a specific truncation of the native sequence, or a desired, specific mutation of the native sequence. If an MBP tag was used, the resulting fusion protein is a hisTag-MBP-BRC4 fusion protein. The hisTag may be on the N-terminus or C-terminus of the fusion protein. Other sequences may encode for tags such as, but not limited to, a MYC tag, FLAG tag, Strep tag, MBP tag, GST tag or any other protein tags known by one of ordinary skill in the art.

Since F-X-X-A interaction is largely a hydrophobic interaction, cells may be lysed using buffers that stabilize hydrophobic interactions. Such buffers may have a high salt concentration such as $(NH_4)_2SO_4$, $K_2PO_4$, sodium acetate, NaCl, or KCl) or a detergent (such as deoxycholate or Triton-X 100). Additional additives to the lysis buffer or in subsequent buffers used in the protein purification process may be glycerol, carbohydrates (such as glucose or sucrose), metal chelators (such as EDTA or EGTA), reducing agents (such as dithiothreitol, dithioerythritol, 2-mercaptoethanol, or tris(2-carboxyethyl)phosphine), ligands (such as ATP, ADP, AMP, or GTP), metal ions or cofactors (such as $Mg^{2+}$, $Ca^{2+}$, $Fe^{2+}$, $Fe^{3+}$, $Mn^{2+}$, $Zn^{2+}$, or $Cu^{2+}$), protease inhibitors (such as pepstatin, leupeptin, or phenylmethanesulfonyl fluoride), or any buffer additive known to one with ordinary skill in the art.

Once the cells co-expressing the RAD51 protein and the hisTag-MBP-BRC4 tagged protein are lysed and clarified, the soluble lysate may be applied to a resin specific to the MBP affinity tag that is part of the hisTag-MBP-BRC4 protein. The MBP tagged protein may be applied to a resin containing immobilized amylose. In an alternative embodiment, a GST tag may be used instead the MBP tag. A GST tag may require a resin containing immobilized glutathione. The RAD51 protein interacts with the F-X-X-A motif in the hisTag-MBP-BRC4 protein thus RAD51 will be bound with the hisTag-MBP-BRC4 protein to the immobilized resin. Following binding, and a subsequent wash step, the BRC4-containing tagged protein is eluted from the resin, for example eluted with maltose, which results in a significant enrichment in the eluate of the hisTag-MBP-BRC4 protein and the RAD51 protein which co-purifies with the hisTag-MBP-BRC4 protein.

Alternatively, once the cells co-expressing the RAD51 protein and the hisTag-MBP-BRC4 tagged protein are lysed and clarified, the soluble lysate may be applied to a resin specific to the 6xHis tag that is part of the hisTag-MBP-BRC4 protein. For example, a resin containing ligands such as immobilized nitrile triacetic acid (NTA), iminodiacetic acid (IDA), or tris(carboxymethyl)ethylene diamine (TED) or a resin that binds divalent metal cations such as $Ni^{2+}$ or $Co^{2+}$ maybe used. The RAD51 protein interacts with the F-X-X-A motif in the hisTag-MBP-BRC4 protein, thus RAD51 will be bound with the hisTag-MBP-BRC4 protein to the immobilized resin. Following binding, and a subsequent wash step, the BRC4-containing tagged protein is eluted from the resin. For example, an imidazole wash results in a significant enrichment in the eluate of the hisTag-MBP-BRC4 protein and the RAD51 protein which co-purifies with the hisTag-MBP-BRC4 protein.

Separating the RAD51 protein from the bound hisTag-MBP-BRC4 protein may be accomplished by utilizing a ligand that provides inherent RAD51 binding, and little to no binding affinity for the hisTag-MBP-BRC4 fusion protein. One example is a resin containing an immobilized ligand that is known to generally mimic DNA molecules. One exemplary ligand is a heparin. Other ligands may be employed that are known to one with ordinary skill in the art with the properties that allow efficient binding to a variety of DNA binding proteins. Before applying the sample, a heparin containing phase requires a salt concentration that should be considered and diluted accordingly (50-100 mM NaCl optimally). By applying the BRC4-containing tagged fusion protein and RAD51 or DMC1 protein containing eluate to heparin, the BRC4-containing tagged fusion protein may remain in the unbound state and flow through the heparin containing phase, or weakly bind to heparin thereby eluting very early in the elution profile as the salt concentration gradually applied to the resin increases. As the salt concentration reaches a relatively high concentration, roughly 500-700 mM NaCl, RAD51 or DMC1 elutes from the heparin ligand, thereby successfully separating RAD51 or DMC1 from its BRC4-containing tagged fusion protein. Chromatography or other methods that involve the use a ligand bound solid support may be used in this isolation step.

The RAD51 protein that eluted from heparin resin may then be applied to a chromatography column filled with size exclusion chromatography (i.e. gel filtration) media in order to remove any remaining contaminants. Examples of a gel filtration resin may be Superdex (for example Superdex 200), Sephacryl (for example S-100 HR), Superose (for example Superose 6), Sephadex (for example Sephadex G-10), or Sepharose (for example Sepharose 4B) variety resins. This final gel filtration step may also serve to exchange the protein into a desired buffer or possibly concentrate the sample. As the RAD51 is generally in a large, multimeric form, it will elute mainly in the void volume of a standard gel filtration column.

In place of heparin, other ion exchange ligands such as a cation exchange or anion exchange can be successfully used to separate RAD51 from the hisTag-MBP-BRC4 protein as well as from other contaminant proteins. RAD51 may bind to an alternative ligand, though the inherit capacity of the chosen affinity tag for the particular ion-exchange resin would have to be taken into consideration.

Also, in place of the BRC4 motif, other BRC motifs, as well as the C-terminal RAD51 binding motif of BRCA2, may be used to initially isolate and/or enrich RAD51 from cell lysate.

For the purification of DMC1, the same principle described above may be employed in place of RAD51. However, not the isolation does not depend on BRC4 repeat as the subtle differences in protein sequence make DMC1 a poor binding partner for a BRC4 repeat.

Recombinant DMC1 protein expression can be done in any expression system of choice (i.e. bacteria, yeast, insect cell, or mammalian cell). The recombinant DMC1 protein is co-overexpressed with a fusion protein wherein the fusion protein includes sequences for an affinity tag (such as MBP or GST), and the BRC4 F-X-X-A repeat motif of the Breast Cancer Susceptibility Protein (BRCA2), and the RAD51 F-X-X-A motif, and an additional tag (such as a polyhistidine tag) may be utilized for recombinant protein purification. If an MBP tag is used in making the fusion protein construct, the resulting fusion protein is a hisTag-MBP-BRC4-RAD51 fusion protein. The sequence for the RAD51 protein may be the full-length, native sequence or a specific truncation of the native sequence, or a desired, specific mutation of the native sequence. The sequence for the co-overexpressed DMC1 protein can be the full-length, native sequence or a specific truncation of the native sequence, or a desired, specific mutation of the native sequence. In an alternate embodiment of the hisTag-MBP-BRC4-RAD51 fusion protein, BCR4 may be substituted by any of BRCA2 1-8 sequence. In yet another embodiment, the MBP sequence in hisTag-MBP-BRC4-RAD51 may be substituted for a different protein tag, for example at GST tag. The 6XHis tag may be on the N-terminus or C-terminus of the fusion protein.

As in the exemplary RAD51 purification method described above, the hisTag-MBP-BCR4-RAD51 fusion protein containing the RAD51 F-X-X-A ATPase domain may be co-overexpressed with the DMC1 protein. To isolate DMC1 from cell lysate, the interaction between DMC1 and the RAD51 F-X-X-A ATPase domain can be exploited to enrich and subsequently purify DMC1. For example, the RAD51 F-X-X-A ATPase domain in the hisTag-MBP-BCR4-RAD51 fusion protein facilitates the interaction with additional DMC1 molecules. When the fusion protein hisTag-MBP-BCR4-RAD51 fusion protein is isolated from clarified lysate, DMC1 will be enriched along with it. Subsequently applying the eluate to a heparin as described for RAD51 will result in the hisTag-MBP-BCR4-RAD51 fusion protein being separated from DMC1.

To diminish the binding capacity of the F-X-X-A ATPase-fusion to heparin, the ATPase domain may be engineered to have its DNA binding loops (L1 and/or L2) removed. Thus, the DMC1 separation via heparin or an equivalent resin may be more efficient.

All of the described methods can be carried out with a BRC repeat mutated in a manner which preserves binding interactions with RAD51 and/or DMC1. Possible mutations include mutations resulting in a W-X-X-A motif, a F-X-X-α-amino butyric acid (U) motif, and a F-X-X-S motif.

Figure 1:
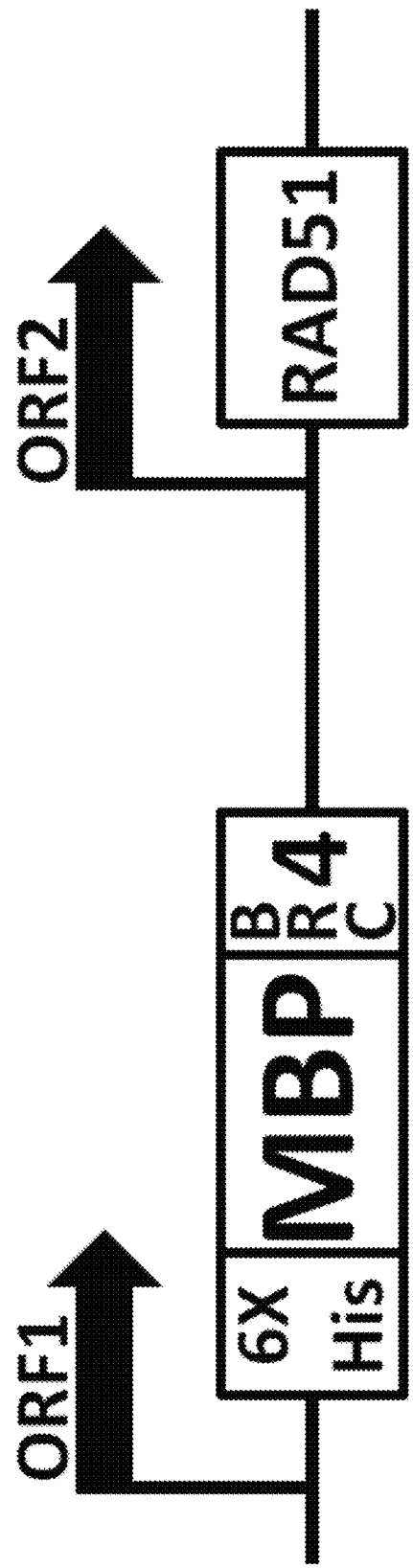
FIG. 1. Diagram representation of vector construct for co-overexpression of 6Xhis-MBP-tagged-BRC4 fusion protein from Open Reading Frame 1 (ORF1) and RAD51 protein from Open Reading Frame 2 (ORF 2).

DETAILED DESCRIPTION OF THE INVENTION (i) Definitions

The following definitions, unless otherwise stated, apply to all aspects and embodiments of the present application.

The present invention contemplates the co-expression and purification of a protein and recombinant protein.

An "oligonucleotide" refers to a single stranded DNA, RNA, or a DNA-RNA hybrid nucleic acid strand that may be approximately 18 to 30 nucleotides in length. Oligonucleotides can hybridize to genetic material such as DNA, cDNA, or mRNA. Oligonucleotides can be labeled at their 5'-terminus via an amino- or thiol-linker or at the 3'-terminus via an amino link with, but not limited to, fluorophores such as Cy3™, Cy5™, fluorescein, quenchers such as Dabcyl or T-Dabsyl, or alternative labels such as biotin and radioisotopes. Labeled oligonucleotides may function as probes to detect the presence of nucleic acids with a complementary nucleic acid sequence. Labeled or unlabeled oligonucleotides may also be used as primers necessary for performing PCR when cloning or detecting the presence of a gene. Oligonucleotides are prepared synthetically by solid-phase synthesis using modified or unmodified 2'-deoxynucleosides (dA, dC, dG, and dT) or ribonucleosides (A, C, G, U).

The terms "protein", "peptide", and "polypeptide" refer to a linear macromolecular polymer of at least two natural or non-natural amino acids covalently linked together by peptide bonds. A protein, peptide, or polypeptide has a free amino group at the N-terminus and a free carboxyl group at the C-terminus unless circular or specifically tagged at the N- or C-terminus. The amino acid sequence of a protein, peptide, or a polypeptide is determined by the nucleotide sequence of a gene. Proteins, peptides and polypeptides may have a primary, secondary, and tertiary structure. At times, the protein, peptide, or polypeptide may also be post-translationally modified with prosthetic groups or cofactors.

The term "gene" refers to a specific DNA sequence that can be transcribed into RNA which can then be translated into a peptide or a polypeptide. Regions in the DNA sequence of a gene may also include regulatory regions, the transcribed sequence for RNA, and the coding sequence with a start and stop codon that is translated into a protein. Transcriptional and translational regulatory regions that control the expression of a gene may include promoters, enhancers, terminators, and in the case of eukaryotic expression a polyadenylation signal.

The term "cloning vector" refers to pieces of nucleic acid that can be used for the insertion and stable preservation of foreign pieces of DNA within an organism. The cloning vector may be a plasmid, bacertiophage, cosmid, bacterial artificial chromosome, or a yeast artificial chromosome. Cloning vectors may be used for creating genomic libraries such as in the invention herein.

A "plasmid" is a vector that refers to an independently replicating circular double-stranded piece of DNA. The plasmid may contain an origin of replication such as the *E. coli* oriC, a selectable antibiotic resistance gene conferring resistance to but not limited to β-lactam, macrolide, and aminoglycosides antibiotics, a promoter sequence under expression control, and a multiple cloning site containing restriction sites which may or may not contain a coding sequence for an antibody like protein described herein.

The plasmid may be an "expression plasmid". Expression plasmids allow for the expression of a cloned gene. An expression plasmid contains an inducible promoter region that allows for the regulation and induction of gene expression of a gene cloned into the plasmid's multiple cloning site, a ribosomal binding site, a start codon, a stop codon, and a termination of transcription sequence.

The term "promoter sequence" is a region of DNA either upstream or downstream from the site of initiation of transcription of a gene. As used herein, a bacterial promoter includes necessary consensus sequences of TTGACA at the −35 and a Pribnow box TATAAT sequence at the −10 position upstream of the start of transcription, and may also contain an UP element upstream of the −35 region.

The term "recombinant protein" refers to a protein that is expressed from an engineered "recombinant DNA" coding sequence. Recombinant DNA combines at least two separate DNA strands into one strand that would not have been normally made in nature. Molecular cloning is used to construct recombinant DNA and may involve the amplification of a DNA fragment of interest and then inserting the fragment into a cloning vector. The recombinant DNA is then introduced into a host organism which is then screened and selected for the presence of the inserted recombinant DNA.

The term "amplification" refers to the act of mass replication of a genetic sequence. Amplification of a genetic sequence may be performed by polymerase chain reaction (PCR) using primers that hybridize to flanking ends of a genetic sequence of interest. Amplification of a genetic sequence may also be performed in vivo by transforming bacteria with a plasmid or transfecting a host cell with a virus that carries the recombinant genetic sequence of interest.

The term "protein expression" refers to the production of protein within a host cell such as a bacteria, yeast, plant, or animal cell. A vector carrying the coding sequence for a recombinant protein under the control of a promoter, such as an expression plasmid, is inserted into a host cell. The promoter controlling the expression of the recombinant gene is then induced and the protein encoded by the recombinant gene is produced within the host cell.

The term "protein purification" refers to a process of purifying a protein and may employ any technique used to separate and isolate a protein of interest to a satisfactory level of purity. Protein purification exploits a protein's various properties such as size, charge, binding affinity, and biological activity. Liquid column chromatography is commonly used in protein purification where a cell lysate containing an expressed protein is passed over a "resin" with particular binding affinity for the protein of interest. A resin is a compound or a polymer with chemical properties that supports the purification of proteins via ion exchange, hydrophobic interaction, size exclusion, reverse phase, or affinity tag chromatography. A protein may also be purified by non-chromatographic techniques such as through the electroporation of protein from an excised piece of a polyacrylamide gel that contained a protein sample of interest.

A "protein tag" refers to an amino acid sequence within a recombinant protein that provides new characteristics to the recombinant protein that assist in protein purification, identification, or activity based on the tag's characteristics and affinity. A protein tag may provide a novel enzymatic property to the recombinant protein such as a biotin tag, or a tag may provide a means of protein identification such as with fluorescence tags encoding for green fluorescent protein or red fluorescent protein. Protein tags may be added onto the N- or C-terminus of a protein. A common protein tag used in protein purification is a poly-His tag where a series of approximately six histidine amino acid residues are added which enables the protein to bind to protein purification matrices chelated to metal ions such as nickel or cobalt. Other tags commonly used in protein purification include chitin binding protein, maltose binding protein, glutathione-S-transferase, and FLAG-tag. Tags such as "epitope tags" may also confer the protein to have an affinity towards an antibody. Common antibody epitope tags include the V5-tag, Myc-tag, and HA-tag.

The terms "fusion protein" or "fused protein" refer to a protein that is coded by a single gene and the single gene is made up of coding sequences that originally coded for at least two or more separate proteins. A fusion protein may retain the functional domains of the two or more separate proteins. Part of the coding sequence for a fusion protein may code for an epitope tag. As described herein for the antibody like protein, a fusion protein may also contain sequences that code for a variety of proteins having varying functional roles based on its application.

The term "protein coding sequence" refers to a portion of a gene that codes for a polypeptide. The coding sequence is located between an ATG initiation of translation codon and the location of a TAG, TAA, or TGA termination of translation codon. Typical to eukaryotic genes, the coding sequence may include the "exons" of a gene, which is the sequence of a gene that is transcribed and translated into a polypeptide, and may exclude the "introns" of a gene, which is the sequence of a gene that is transcribed but not translated into a polypeptide.

The term "transformation" refers to a process of introducing exogenous genetic material into a bacterium by methods employing membrane permeability via chemical or electrical means. Performing a transformation involves adding genetic material, such as a plasmid, to an aliquot of competent bacterial cells, such as E. coli, and allowing the mixture to incubate on ice. The bacterial cells are then either electroporated or placed at 42° C. for approximately 1 minute and then returned to incubate on ice. The bacterial cells are then grown on an agar plate overnight until colonies are visible. The agar plate may contain antibiotic or nutrient conditions for colony selection.

The term "transfection" refers is the process of deliberately introducing nucleic acids into cells. The term is often used for non-viral methods in eukaryotic cells. It may also refer to other methods and cell types, although other terms are preferred: "transformation" is more often used to describe non-viral DNA transfer in bacteria, non-animal eukaryotic cells, including plant cells. In animal cells, transfection is the preferred term as transformation is also used to refer to progression to a cancerous state (carcinogenesis) in these cells. "Transduction" is often used to describe virus-mediated DNA transfer. *Nature Methods* 2, 875-883 (2005).

The term "Western blot" refers to an analytical technique used to determine the presence of a polypeptide. A Western blot is performed by initially separating proteins on a sodium dodecyl sulfate polyacrylamide gel (SDS-PAGE), and then electro-transferring the separated proteins onto a filter membrane such as a nitrocellulose of PVDF membrane. The membrane is then incubated with a blocking buffer that may contain a blocking agent such as bovine serum albumin or non-fat dry milk. The membrane is then incubated with a primary antibody that is specific for the polypeptide of interest. The primary antibody is washed off from the membrane and the membrane is then incubated with a secondary antibody that is conjugated to a compound or an enzyme that allows for detection and visualization.

The term "homologous sequence" refers to an amino acid or nucleotide sequence that is at least 70% to 99% homologous to a corresponding reference sequence. Sequences that are 90% identical have no more than one different amino acid per 10 amino acids in the reference sequence. The percentage of homology between two or more sequences may be identified using a homology algorithm of Smith and Waterman (1970) Adv. Appl. Math 2:482c, Needleman and Wunsch (1970) J. Mol. Biol. 48:433, or Pearson and Lipman (1988) Proc. Natl. Sci. 85:2444. The methods of sequence alignment are known to those in the art. A computer based program employing the mentioned or alternative sequence comparison algorithms may be used such as BLAST as described in The NCBI Handbook (2002) or ClustalOmega as described in Sievers et. al. Mol. Sys. Bio. 7:539 (2011).

The terms "antibody" and "immunoglobulin" are interchangeable and refer to a polypeptide tetramer macromolecule that recognizes and binds, with high affinity and precision, to a binding site referred to as an "epitope" on an antibody target molecule referred to as an "antigen". Antibodies are made up of two identical "heavy chains" and two identical "light chains" referring to the size of each of the individual polypeptide components of an antibody. Each chain is composed of a variable domain and a constant domain, such as the variable heavy and light chains, $V_H$ and $V_L$, respectively, and the constant heavy and light chains, $C_H$ and $C_L$, respectively. The heavy and light chains are interconnected with disulfide bonds to form a Y like structure. The antibody Y like structure can be separated into two regions; the top Fab region and the bottom Fc region. The Fab region contains the variable domains and is responsible for antigen recognition, whereas the Fc region is responsible for inducing effector functions and cellular responses. A review of antibody characteristics and antibody structure is provided in Antibodies: A Laboratory Manual, Second Edition, Cold Spring Harbor Laboratory Press (2013).

The term "fluorescent label" refers to a "fluorophore" that may be covalently attached to a polypeptide or a nucleic acid. Fluorophores absorb light energy at a specific excitation wavelength and re-emit light energy at a specific lower emission wavelength as described by Lakowicz J R. in Principles of Fluorescence Spectroscopy $3^{rd}$ ed. Springer Publishing (2006). Fluorescent labels allow for the detection and localization of a labeled polypeptide or nucleic acid through the use of a microscope that detects fluorescence, a flow cytometer, or any other instrument capable of detecting fluorescence. The labeling, detection, and localization of fluorescently labeled proteins and has been described in detail by Modesti M., Meth. in Mol. Bio. 783:101-20 (2011) and Giepmans et. al., Science 312:5771 (2006). Common fluorophores include but are not limited to Alexa Fluor®, Cy®3 and Cy®5, FITC, TRITC, DAPI, APC, R-PE, and Qdot® as provided by Life Technologies in their Fluorophore Selection guide (www.lifetechnologies.com) and Thermo Scientific (www.piercenet.com).

The term "conserved sequence" refers to a sequence of nucleotides in DNA or RNA, or amino acids in a polypeptide, that are similar across a range of species. Conserved sequences are represented by a nucleotide or an amino acid that occurs at the highest frequency at a particular site in a homologous gene or protein from the same or different species. The term "non-conserved sequence" refers to a sequence of nucleotides or amino acids in a gene or protein that are not conserved and that have a higher variability than conserved sequences.

The term "recombinase protein" refers to any protein or enzyme that is involved in genetic recombination. Recombinase proteins may be involved in various types of genetic recombination events and DNA repair process, such as excision, insertion, inversion, translocation, homologous recombination, or cassette exchange. Recombinase proteins may belong to any family of recombinases, for example, Cre recombinase, Hin recombinase, Tre recombinase, FLP recombinase, Rec recombinase, and integrase family of recombinsases.

The term "two step PCR" refers to a PCR method where a sequence alteration such as a point mutation or introduction/deletion is performed. In a two-step PCR method, a primer set containing the specific DNA alteration and at least 10 bases of 5' complementary overlap is used. The mutagenic primer corresponding to the sense strand of the gene is used as a forward primer coupled with an outer flanking reverse primer. In another concurrent reaction, the corresponding mutagenic "antisense" primer is used a reverse primer with an outer flanking forward primer. The outer primers flanking the DNA of interest should anneal outside the cloning sites to be used for re-introducing the altered DNA back into the vector of choice, or include sequence for required restriction sites if a different destination vector is to be desired.

The term "ligand" refers to any functional group of molecules that form a coordinated interaction with a protein. For example, heparin operates as a ligand with affinity for biomolecules including proteins, lipoproteins, DNA binding proteins, and steroid receptors. A ligand can be immobilized or "coupled" to a solid support such as a base matrix by coupling the ligand via chemical bonds to the base matrix. For example, heparin may be coupled to a Sepharose base matrix. A ligand may be any affinity functional group known to one of ordinary skill in the art. Ligands may be immobilized on resin such as resins used in column chromatography or onto surfaces such as those used in enzyme linked immunosorbent assays (ELISAs).

(ii) Construction of Expression Vectors

The present invention provides for the products and method involving the purification of recombinase proteins, in particular RAD51 and DMC1 proteins, SEQ ID 18 and SEQ ID 21, respectively, of the Rec recombinase family. The genes that encode for the RAD51 or DMC1 may be amplified from any organism, such as from human (for example SEQ ID 12 and SEQ ID 15, respectively) yeast, or bacteria using PCR.

In one exemplary embodiment the gene sequence (SEQ ID 12) coding for the full length human RAD51 protein (SEQ ID 18) may be amplified by PCR, for example by using a forward primer (SEQ ID 1) and a reverse primer (SEQ ID 2), wherein SEQ ID 1 and SEQ ID 2 are ATATATA-CATATGGCAATGCAGATGCAGCTTG (RAD51-Nde-I_Fwd) and TATATCCTAGGTTATTAGTCTTTGG-CATCTCCCACTCC (RAD51-AvrII Rev), respectively. The amplified RAD51 PCR product may be subsequently cloned between the NdeI and AvrII restriction sites within an expression. Alternative restriction sites sequences may be designed or included in the primers. In yet another embodiment the gene sequence for RAD51 including introns and exons may be cloned. The cloned RAD511 gene may be of the full-length sequence as taught in SEQ ID 12 or of any truncated sequence thereof. Alternatively, the cloned full length or truncated RAD51 gene may be tagged at the N- or C-terminus with one or more tags. In yet an alternative embodiment, the cloned RAD51 gene may be mutated at one or more nucleotides.

In another exemplary embodiment the gene sequence (SEQ ID 15) coding for the full length human DMC1 protein (SEQ ID 21) may be amplified PCR, for example by using a forward primer (SEQ 3) and a reverse primer (SEQ 4), wherein SEQ3 and SEQ 4 are AGTTGCCCATAT-GAAGGAGGATCAAGTTGTGG (DMC1-NdeI-Fwd) and GTACAACCTAGGTTATTACTCCTTCGCATCCCCAAT-TCC (DMC1-AvrII-Rev), respectively. The amplified DMC1 PCR product may be subsequently cloned between the NdeI and AvrII restriction sites within an expression vector. Alternative restriction sites sequences may be designed or included in the primers. In yet another embodiment the gene sequence for DMC1 including introns and exons may be cloned. The cloned DMC1 gene may be of the full-length sequence as taught in SEQ 15 or of any truncated sequence thereof. Alternatively, the cloned full length or truncated DMC1 gene may be tagged at the N- or C-terminus with one or more tags. In yet an alternative embodiment, the cloned DMC1 gene may be mutated at one or more nucleotides.

In one vector construct embodiment, the pRSFDuet-1 (Novagen) dual expression vector may be used for cloning and co-overexpression of inserted sequences. DNA sequences may be inserted into the multiple cloning site of pRSFDuet-1, the multiple cloning site of pRSFDuet-1 is shown in SEQ ID 24. Any dual expression vector may be used. In a preferred embodiment, the sequence for a 6X Histidine-tagged Maltose Binding Protein (MBP) may be inserted between the NcoI and AscI sites of the first open reading frame (ORF1) in the RSFDuet-1 expression vector; designated as the pRSF-Duet1-6XhisMBP vector. In another embodiment, the 6XHis or MBP tags may be substituted by alternative tags, such as a Glutathione S-transferase (GST) tag.

Sequences encoding the BRCA2 BRC4 peptide may be PCR amplified with forward primer SEQ 5 and reverse primer SEQ 6, ATTGGGCGCGCCTGGAAAA CCTGTAT-TTTCAGGGATCCAAAGAACCGACCCTGCTG (AscI-BamHI-BRC4-FWD) and AGCTGCGGCCGCTTATT-AGTCGAACAGGTTTTTAAC (BRC4_D1547-NotI-REV), respectively, and subsequently ligated between AscI and NotI in the pRSF-Duet1-6XhisMBP vector; resulting in a pRSF-Duet1-6Xhis-MBP-BRC4 vector that encodes a 6Xhis-MBP-BRC4 fusion protein (SEQ ID 22) transcribed by Open Reading Frame 1 (ORF1). The gene sequence for the 6Xhis-MBP-BRC4 fusion protein is represented by SEQ ID 16, whereas the protein sequence for the 6Xhis-MBP-BRC4 fusion protein is represented by SEQ ID 22.

To the pRSF-Duet1-6Xhis-MBP-BRC4 vector, the RAD51 gene sequence (SEQ ID 12) amplified by SEQ 1 and SEQ 2 primers may be subsequently cloned between the NdeI and AvrII sites of ORF2, producing a pRSF-Duet1-6Xhis-MBP-BRC4 co hRAD51 cloned construct as shown in FIG. 1. The pRSF-Duet1-6Xhis-MBP-BRC4 co hRAD51 construct may be transformed into a cell that permits co-overexpression of ORF1 and ORF2, thus co-overexpressing both the 6Xhis-MBP-BRC4 fusion protein (SEQ ID 22) from ORF1 and the RAD51 protein (SEQ ID 18) from ORF2.

In an alternative embodiment, SEQ ID 16 (the DNA sequence that codes for the 6Xhis-MBP-BRC4 fusion protein) and SEQ ID 12 (the DNA sequence that codes for the RAD51 protein) may be inserted into any dual expression plasmid under the control of separate promoters or the same promoter. An internal ribosomal entry site (IRES) sequence may be inserted between the 6Xhis-MB-BRC4 and RAD51coding sequences. In an alternative embodiment, a "self cleaving" P2A element (such as the T2A, P2A, E2A, F2A protein sequences) may be inserted between the 6Xhis-MB-BRC4 and RAD51coding sequences. In yet an alternative embodiment, the DNA sequence that codes for the 6Xhis-MBP-BRC4 protein and the DNA sequence that codes for the RAD51 protein may be inserted into separate expression plasmids that are in turn transformed into a single cell. The 6Xhis-MBP-BRC4 fusion protein and the RAD51 protein may be expressed in the same organism or in separate organisms wherein the cell lysate from each organism may be later combined for purification. Alternative versions of SEQ ID 16 and SEQ ID 12 that maintain the functionality of the translated protein product as known by one of ordinary skill in the art may also be constructed.

Figure 10:
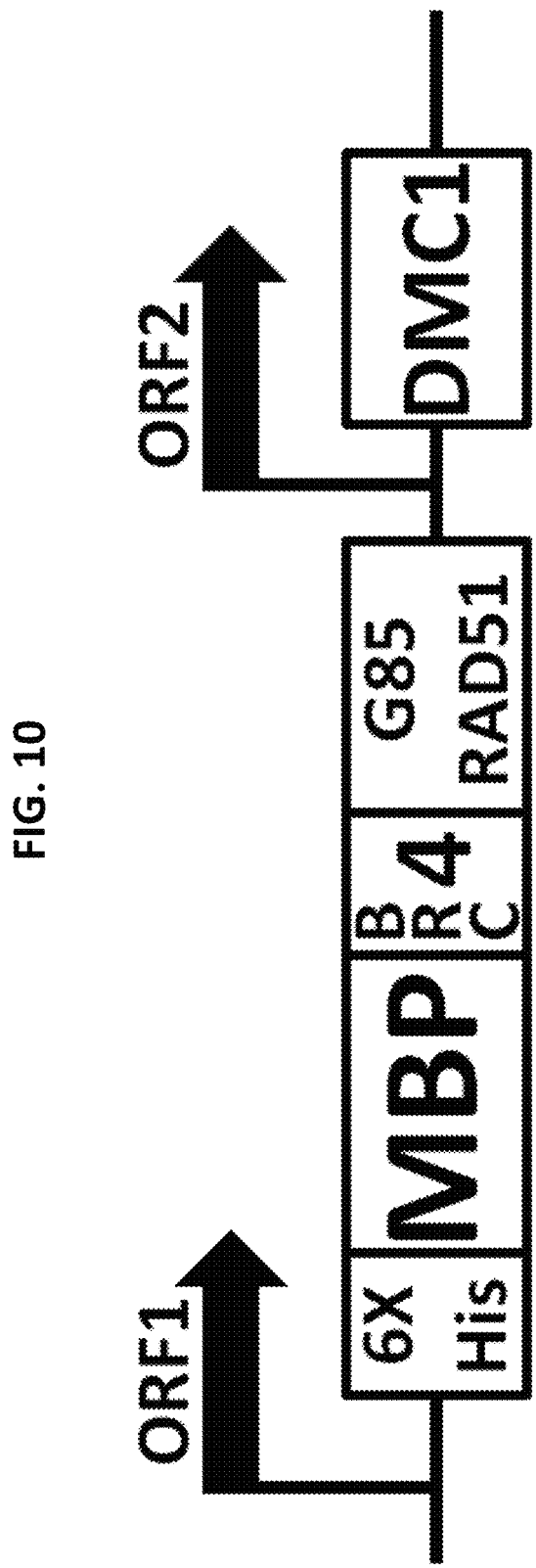
FIG. 10. Diagram representation of vector construct for co-overexpression of 6Xhis-MBP-tagged-BRC4-G85RAD51 ATPase domain fusion protein from ORF1 and DMC1 protein from ORF2.

In yet another embodiment, a dual expression vector may be constructed with a cloned 6Xhis-MBP-BCR4-G85RAD51 fusion protein for expression in a first ORF and DMC1 for expression in a second ORF, as shown in FIG. 10, for example in the dual expression vector pRSFDuet-1. To construct the 6Xhis-MBP-BCR4-G85RAD51 fusion protein construct, RAD51 residues 85-339 may be amplified from a plasmid or genome encoding the RAD51 gene, for example the human RAD51 gene with SEQ 7 and SEQ 8 primers, ACTGCAACTGAATTCCACCAACGTCGCTCAGAGA TCATACAGATTACTACTGG (3xtgs-Rad51G85-fwd) and AGCTGCGGCCGCTTA TCAGTCTTTGGCATCTCC-CACTCC (Rad51-NotI-rev), respectively. SEQ ID 14 represents the gene sequence for human RAD51 residues 85-339. SEQ ID 20 represents the protein sequence for human RAD51 residues 85-339.

BRCA2 residues 1517-1547 may be amplified from plasmid encoding the human BRCA2 gene using SEQ 9 and SEQ 10 primers, GAATAGGATC-CAAAGAACCGACCCTGCTG (BamHI-BRC4-fwd) and GGAAT-TCAGTTGCAGTGGTAAAGCCAGAGCCAGTGCTGCC AGTGCTGCCAGTGTC GAACAGGTTTTTAAC (3xtgsBRC4-rev), respectively. The two products may be annealed using a 2-step PCR and amplified by flanking SEQ 11 primer; BamHI-BRC4-fwd and Rad51-NotI-rev (AGCTGCGGCCGCTTATCAGTCTTTGGCATCT CCCACTCC). The resulting product encodes the BRC4 motif of BRCA2 fused to the N-terminal end of Rad51$_{85-339}$ via a 3XThr-Gly-Ser linker, which is cloned into the BamHI & NotI sites of tev sites of ORF1 of pRSF-Duet1-6Xhis-MBP to produce pRSF-Duet1-6Xhis-MBP-BRC4-G85RAD51. The pRSF-Duet1-6Xhis-MBP-BRC4-G85RAD51 expression vector expresses the 6XHis-MBP-BRC4-G85RAD1 fusion protein from ORF1. SEQ ID 17 represents the gene sequence for the 6XHis-MBP-BRC4-G85RAD1 fusion protein. SEQ ID 23 represents the protein sequence for the 6XHis-MBP-BRC4-G85RAD1 fusion protein. SEQ ID 13 represents the gene sequence for BRC4. SEQ ID 19 represents the protein sequence for BRC4.

Figure 11:
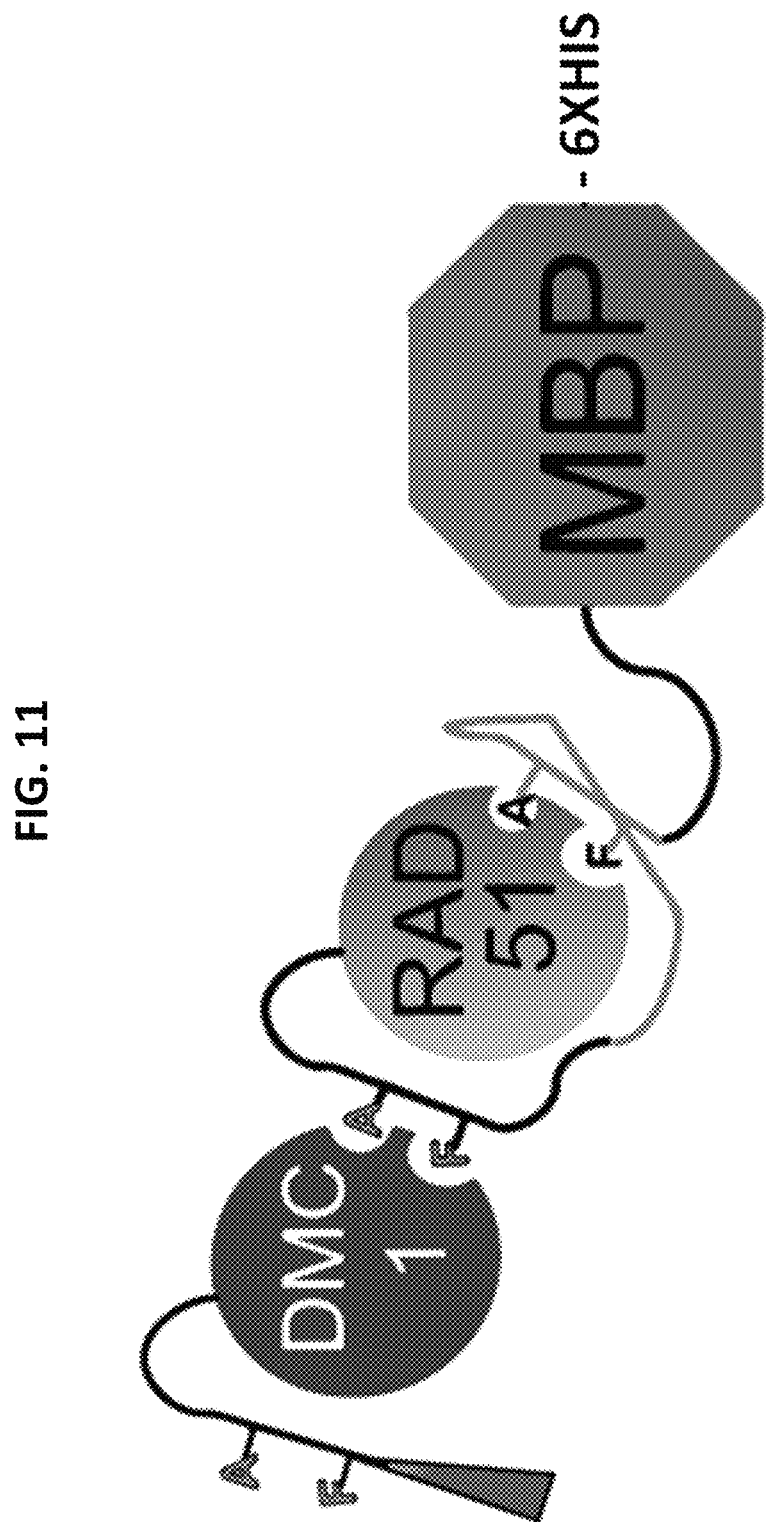
FIG. 11. Representation of DMC1 protein interacting with the G85RAD51 F-X-X-A motif in the 6Xhis-MBP-tagged-BRC4-G85RAD51 ATPase domain fusion protein.

The DMC1 gene (SEQ ID 15) amplified by primers SEQ 3 and SEQ4 may be ligated between the NdeI and AvrII sites of the $2^{nd}$ ORF of pRSF-Duet1-6Xhis-MBP-BRC4-G85RAD51, creating an expression vector (of pRSF-Duet1-6Xhis-MBP-BRC4-G85RAD51 co DMC1) wherein the 6XHis-MBP-BRC4-G85RAD1 fusion protein (SEQ ID 23) may be co-overexpressed with DMC1 protein (SEQ ID 21) as shown in FIG. 10. Once the DMC1 protein and the 6XHis-MBP-BRC4-G85RAD1 fusion protein are co-overexpressed, the DMC1 protein interacts with the G85RAD51 F-X-X-A repeat motif of the ATPase domain in the 6XHis-MBP-BRC4-G85RAD1 fusion protein as shown in FIG. 11.

In an alternative embodiment, the DNA sequence (SEQ ID 17) that codes for the 6XHis-MBP-BRC4-G85RAD1 fusion protein and the DNA sequence (SEQ ID 15) that encodes for the DMC1 protein may be inserted into any dual expression plasmid under the control of separate promoters or the same promoter. For example, an internal ribosomal entry site (IRES) sequence may be inserted between the 6Xhis-MBP-BRC4-G85RAD51 and DMC1 coding sequences. In an alternative embodiment, a "self cleaving" P2A element (such as the T2A, P2A, E2A, F2A protein sequences) may be inserted between the 6Xhis-MB-BRC4 and RAD51coding sequences. In yet an alternative embodiment, the DNA sequence that codes for the 6XHis-MBP-BRC4-G85RAD1 fusion protein and the DNA sequence that codes for the DMC1 protein may be inserted into separate expression plasmids that are in turn transformed into a single cell. The 6XHis-MBP-BRC4-G85RAD1 fusion protein and the DMC1 protein may be expressed in the same organism or in separate organisms wherein the cell lysate from each organism may be later combined for purification.

Any nucleotide sequence encoding for a BRC4 repeat comprising the F-X-X-A motif to be used in a vector construct may be mutated in any manner which preserves binding interactions with RAD51 and/or DMC1.

In certain embodiments, the F-X-X-A motif is mutated to be comprised of alternate amino acids which maintain binding interactions with RAD51 and/or DMC1. For example, in one embodiment the phenylalanine in the F-X-X-A motif may substituted for a tryptophan resulting in a W-X-X-A motif (SEQ ID 25).

In an alternative embodiment the alanine in the F-X-X-A motif may substituted for a glycine resulting in a F-X-X-G motif (SEQ ID 30).

In an alternative embodiment the phenylalanine in the F-X-X-A motif may substituted for a tryptophan and the alanine in the F-X-X-A motif may substituted for a glycine resulting in a W-X-X-G motif (SEQ ID 31).

In an alternative embodiment, the alanine in the F-X-X-A motif may be substituted for a serine resulting in a F-X-X-S motif (SEQ ID 26). Studies using molecular models of BRC motifs have predicted that such a substitution might enhance binding activity. Nomme, Julian et al. Journal of medicinal chemistry vol. 53, 15 (2010): 5782-91.

In an alternative embodiment the phenylalanine in the F-X-X-A motif may substituted for a tryptophan and the alanine in the F-X-X-A motif may substituted for a serine resulting in a W-X-X-S motif (SEQ ID 32).

The alternate amino acids are included as examples of the present invention and are not meant to be limiting.

A person having ordinary skill in the art will recognize that the invention can be practiced with other amino acid substitutions which preserve binding interactions with RAD51 and/or DMC1.

F and A side chains in the F-X-X-A motif are expected to make contacts with hydrophobic pockets on the core catalytic domain of RAD51. Rajendra et al. Nucleic Acids Research (2010) 38(1):82-96. Therefore, a person having ordinary skill in the art will recognize that there is a greater likelihood of preserving binding interactions when substituting the hydrophobic residue, phenylalanine (F), which plugs into a deep hydrophobic pocket located in the globular ATPase domain, with another hydrophobic residue.

In certain embodiments, the F-X-X-A motif is mutated to be comprised of non-proteinogenic and/or synthetic amino acids. For example, in one embodiment, the alanine in the F-X-X-A motif is substituted for an α-amino butyric acid (U) resulting in an F-X-X-U motif. Numerous non-proteinogenic amino acids are known in the art. Walsh et. al., Angew Chem Int Ed Engl., 52(28): 7098-7124 (2013). A person having ordinary skill in the art will recognize that the invention can be practiced with other non-proteinogenic and synthetic amino acid substitutions which preserve binding interactions with RAD51 and/or DMC1.

The F-X-X-A motif may include post-translational modifications and/or mutations with post-translational modifications in a manner which preserves or creates binding interactions with RAD51 and/or DMC1. Mutations in the F-X-X-A motif which result in a loss of binding interactions with RAD51 and/or DMC1 may be may be post-translationally modified to restore binding interactions.

(iii) Purification of RAD51

All recombinant protein expression may be initiated from fresh overnight transformation of E. coli strain BL21, harboring the pRARE plasmid (chloramphenicol resistance), with the co-overexpression plasmid (for example, with the pRSF-Duet1-6Xhis-MBP-BRC4 co RAD51 vector). An entire plate of freshly formed colonies is then scraped and used to seed a starter culture (Turbo Broth culture medium—Athena Enzyme Systems) supplemented with the appropriate antibiotic (routinely both kanamycin and chloramphenicol). A starter culture of may be prepared in an orbital shaker (shaking at an rpm of 180-200 rpm at 37° C.) that is grown to reach an $OD_{600} \geq 1.0$. A volume of the dense starter culture is then used to seed each liter of culture grown (for example 1 L Turbo broth, in 2 L dimpled shake flasks, 8 L total) and allowed to reach $OD_{600} \geq 1.0$. Any volume of culture may be grown for overexpression. At $OD_{600} \geq \sim 1$, over-expression is induced by addition of IPTG, for example a concentration of 200 μM IPTG may be used. The recombinant proteins, such as 6Xhis-MBP-BRC4 fusion protein and the RAD51 protein are overexpressed upon the addition of IPTG. After induction the cell cultures may be grown for an appropriate amount of time to overexpress protein from the induced promoter. For example, cells may be grown for 3 hours at 37° C. while shaking or for 15 hours or overnight at 15° C. while shaking.

Once the 6Xhis-MBP-BRC4 fusion protein and the RAD51 protein are overexpressed, the cells are harvested. Harvesting of cell cultures may be performed by centrifugation, for example centrifugation at 4,200 rpm for 30 minutes at 4° C. The cell pellet may then be lysed in a stabilizing buffer or in cell lysis buffer. An example of cell lysis buffer is 20 mM Tris pH 8.0, 500 mM NaCl, 20 mM imidazole. Additives such as carbohydrates, lysozyme, detergents, reducing agents, or protease inhibitors (such as SIGMAfast™ EDTA-free Protease inhibitor tablets) may be added to the lysis buffer. Cell lysis may be performed using any cell lysis method known by one of ordinary skill in the art. For example, cells may be lysed via a lysis buffer, French Press, sonication, high pressure homogenization (for example an Avestin EmulsiFlex-C5 high pressure homogenizer), jet milling, bead milling, or freeze thaw cycles. In a preferred embodiment, cells are lysed by flash freezing in liquid $N_2$.

The cell lysate may be filtered or centrifuged to separate insoluble cell debris and precipitated debris from soluble protein such as the 6Xhis-MBP-BRC4 fusion protein and the RAD51 protein. In a preferred embodiment, the cell lysate may be centrifuged at 30,000 g for 1 hour at 4° C. After centrifugation, the supernatant may be passed through a filter, for example a 5 μm filter, to remove any remaining insoluble particles in preparation for column chromatography. After centrifugation and/or filtration, the soluble protein (referred to as the cell extract), is applied to a chromatography resin, for example a resin specific to the affinity tag that is fused to the BRC4 repeat motif.

Figure 2A:
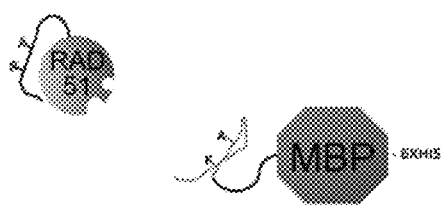
FIG. 2A. Representation of 6Xhis-MBP-tagged-BRC4 and RAD51 proteins.
Figure 2B:
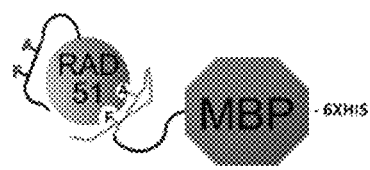
FIG. 2B. Representation of the F-X-X-A motif in the 6Xhis-MBP-tagged-BRC4 fusion protein interacting with RAD51.
Figure 3:
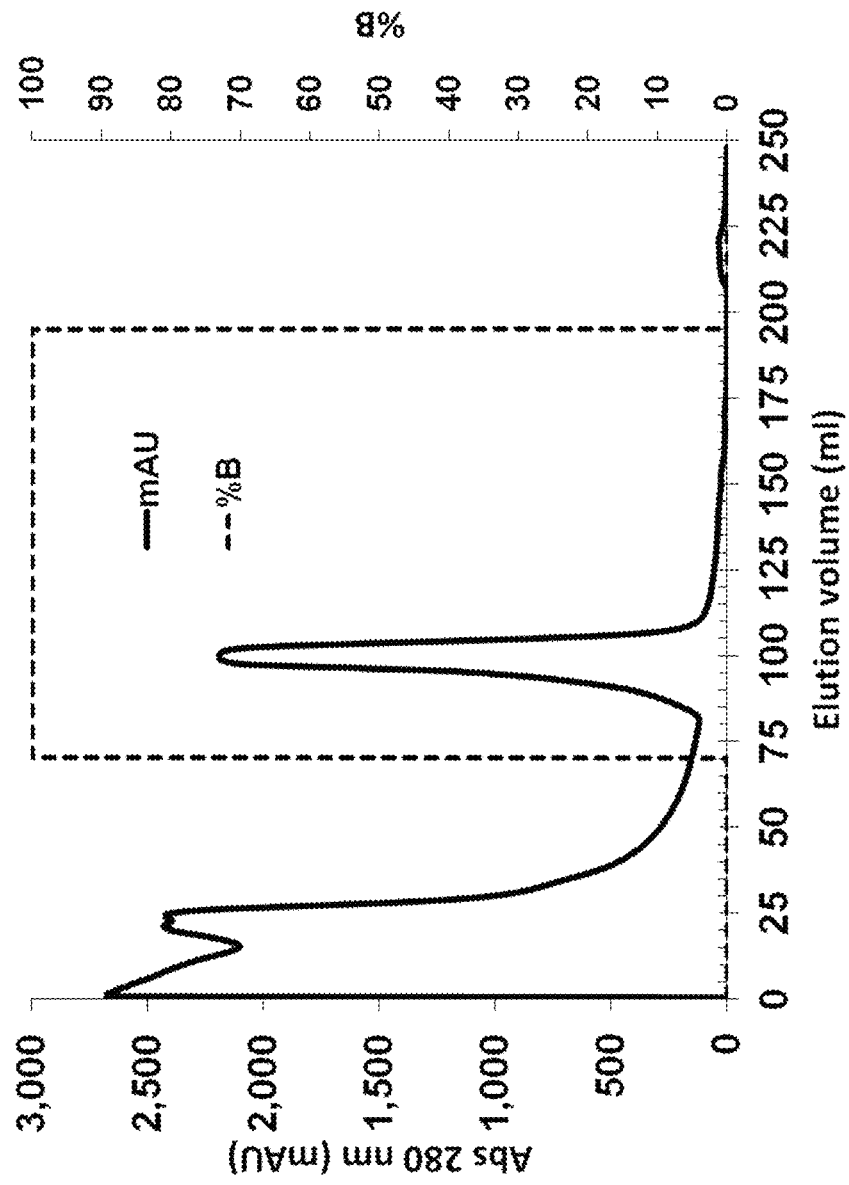
FIG. 3. Elution profile of RAD51 protein purification via $Ni^{2+}$-NTA affinity resin using a step gradient of increasing Imidazole concentration (% B) as the eluent.

The co-overexpressed 6Xhis-MBP-BRC4 fusion protein and the RAD51 protein shown in FIG. 2A interact and form protein-protein bonds with each other as shown in FIG. 2B, permitting for their co-purification. For example, purification of the 6Xhis-MBP-BRC4 fusion protein and RAD51 protein from cell extract may be achieved by applying the cell extract to a resin containing immobilized NTA resin, such as Sepharose HP Hi-Trap™ resin (GE Healthcare Life Sciences), charged with $Ni^{2+}$. A purification system, such as an ÄKTA Protein Purification System (GE Healthcare Life Sciences), may be used for protein purification. Alternatively, the tagged fusion protein and recombinase may be purified using an immobilized ligand. The 6X histidine tag in the 6Xhis-MBP-BRC4 fusion protein binds to the $Ni^{2+}$-NTA resin while concurrently the BRC4 motif binds to the RAD51 protein. The bound proteins may be washed with a wash buffer, for example a wash buffer containing 20 mM Tris pH 8.0, 500 mM NaCl, 20 mM Imidazole. The 6Xhis-MBP-BRC4 fusion protein along with the RAD51 protein may then be eluted from the $Ni^{2+}$-NTA resin using increasing concentration of imidazole as shown in FIG. 3, wherein the mAU peak at 100% B is the elution of the 6Xhis-MBP-BRC4 fusion protein bound to the RAD51 protein. The elution buffer may be 20 mM Tris pH 8.0, 500 mM NaCl, 200 mM imidazole.

Figure 4:
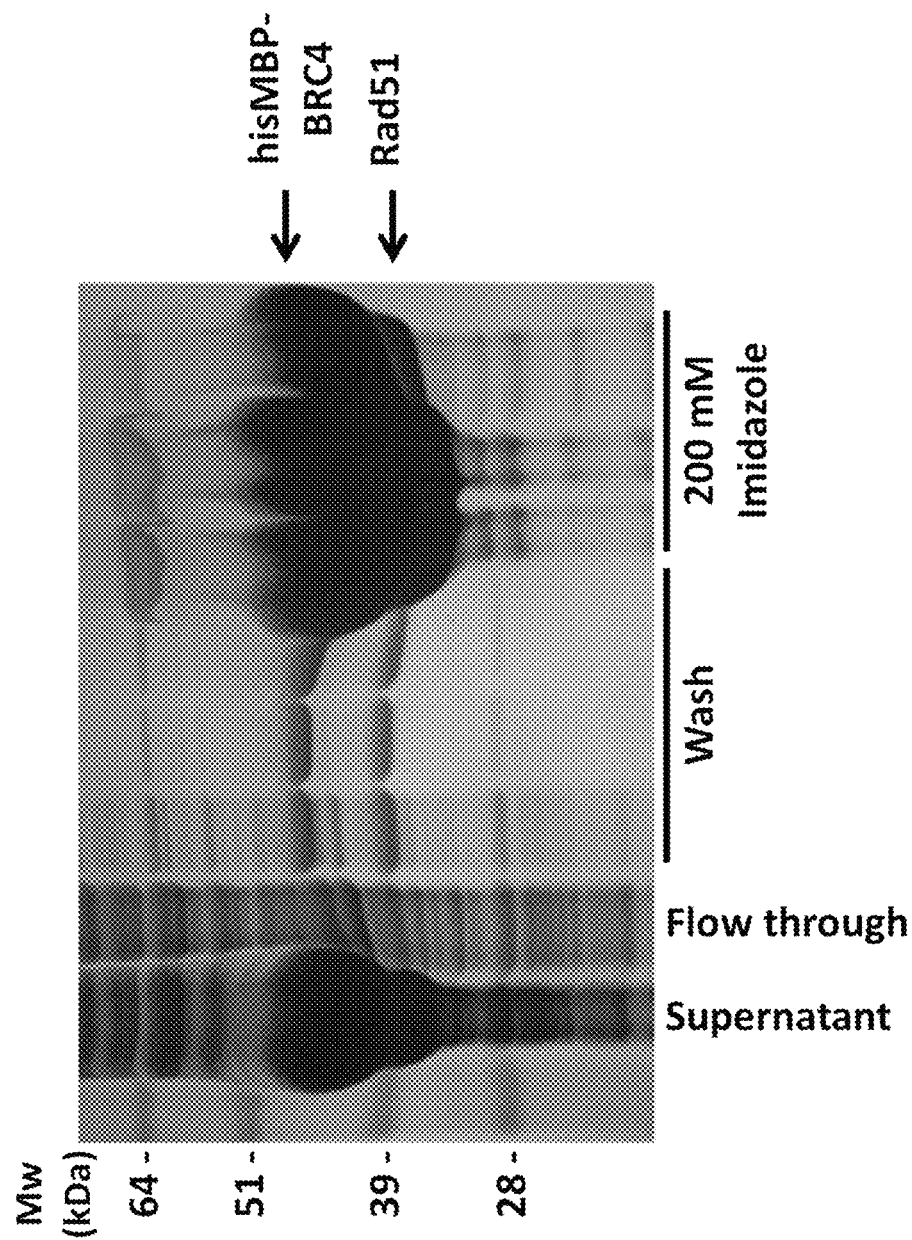
FIG. 4. Coomassie stained SDS-PAGE gel of various elution fractions obtained in RAD51 purification via the $Ni^{2+}$-NTA affinity resin shown in FIG. 3.

FIG. 4 is a Coomassie stained SDS-PAGE gel of various elution fractions obtained from the $Ni^{2+}$-NTA affinity chromatography shown in FIG. 3. FIG. 4 shows that the RAD51 protein bound to the 6Xhis-MBP-BRC4 fusion protein co-eluted in the 200 mM imidazole fraction. Peak fractions containing the RAD51 protein bound to the 6Xhis-MBP-BRC4 fusion protein may be pooled together.

In one embodiment, the pooled fractions containing the RAD51 protein bound to the 6Xhis-MBP-BRC4 fusion protein may then be loaded onto an amylose resin that binds to MBP. The 6Xhis-MBP-BRC4 fusion protein (along with the associated RAD51 protein) binds to the amylose resin. The bound protein my then be washed with wash a wash buffer, for example 20 mM Tris pH 8.0, 500 mM NaCl. Bond protein may then be eluted with elution buffer, for example with 20 mM Tris, pH 8.0, 500 mM NaCl, and 20 mM maltose. In another embodiment, if the fusion protein construct was designed with an alternative protein tag, for example a GST tag, then an alternative affinity resin may be used specific for the alternative tag, for example glutathione Sepharose resin wherein glutathione would be used to elute bound tagged fusion protein along with proteins associated via protein-protein to the fusion tagged protein.

In another embodiment, following elution of the 6Xhis-MBP-BRC4 fusion protein and RAD51 protein from the $Ni^{2+}$-NTA affinity resin, the pooled fractions may be processed by exchanging the sample buffer into a low salt buffer, for example by overnight dialyzing the pooled fractions using a dialysis membrane (for example a 6,000-8000 MWCO dialysis membrane) at 4° C. The said low salt buffer may be Tris pH 8.0, containing 50 mM NaCl.

In yet another embodiment, following elution of the 6Xhis-MBP-BRC4 fusion protein and RAD51 protein from the Ni$^{2+}$-NTA affinity resin, the pooled fractions may be diluted with a buffer, for example diluted 5-fold with 20 mM Tris pH 8.0, resulting in a sample with a NaCl concentration of near 100 mM.

Figure 5:
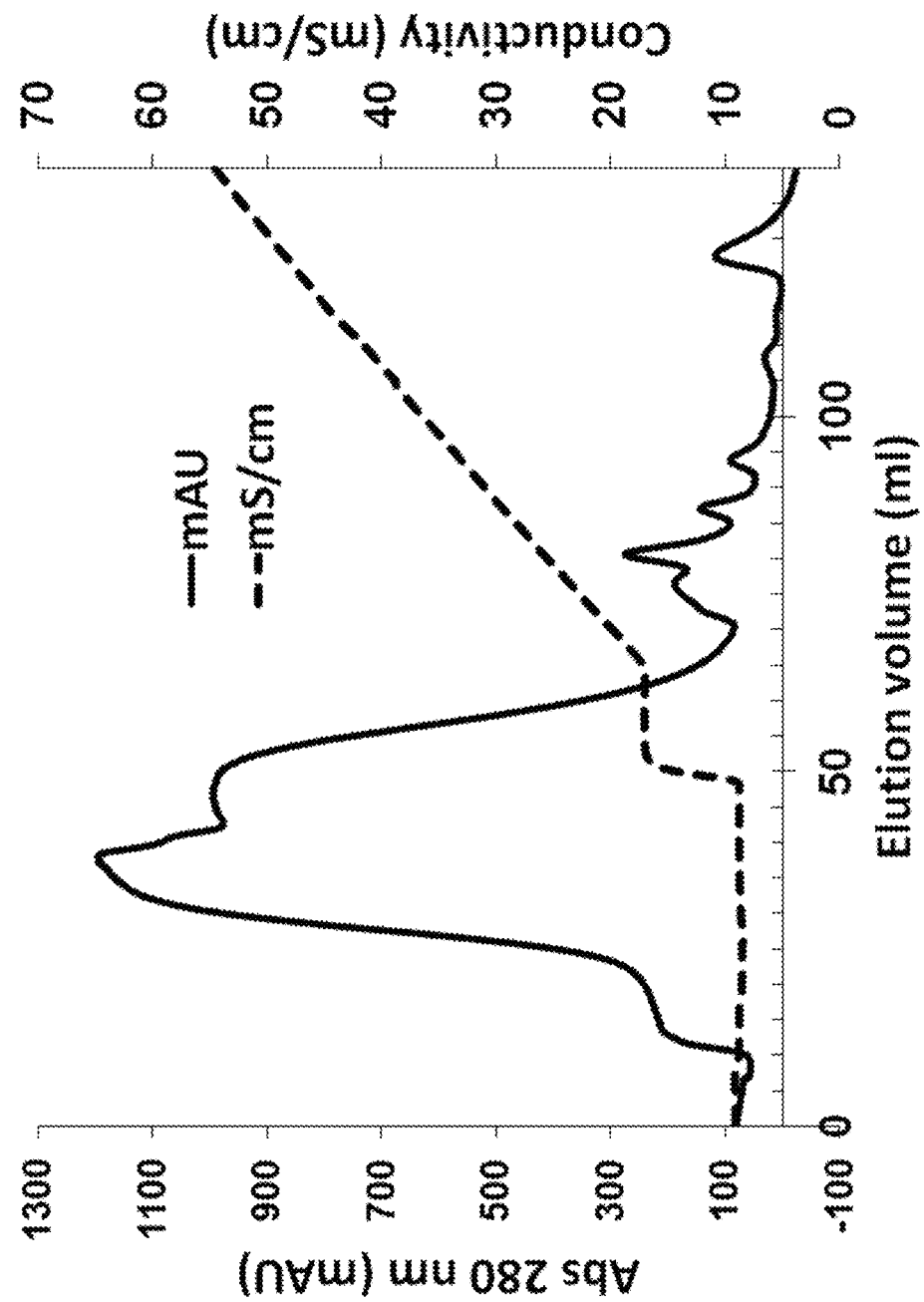
FIG. 5. Elution profile of RAD51 protein purification via affinity to heparin using a step and gradual increasing NaCl concentration as the eluent.

The dialyzed protein sample in low salt buffer may then be applied to a chromatography resin containing an immobilized molecule that is known to generally mimic DNA molecules. One exemplary molecule is the heparin ligand which is known to one with ordinary skill in the art to efficiently bind to a variety of DNA binding proteins. For example, the dialyzed protein may be applied to a Heparin Sepharose HiTrap™ HF resin (GE Healthcare Life Science). The RAD51 protein has biding specificity to the heparin ligand and will bind to the heparin ligand along with the bound 6Xhis-MBP-BRC4 fusion protein. Increasing the NaCl concentration, for example from 0.1 to 1.0 M, will elute proteins bound to the heparin ligand. The heparin ligand with bound protein may be washed with a wash buffer, for example 20 mM Tris pH 8.0 and 200 mM, followed by elution with a linear 0.2 M-0.7 M NaCl gradient as shown in FIG. 5. The 6Xhis-MBP-BRC4 fusion protein will elute early in the NaCl gradient, while RAD51 will elute near 600 mM NaCl as shown in FIG. 5.

Figure 6:
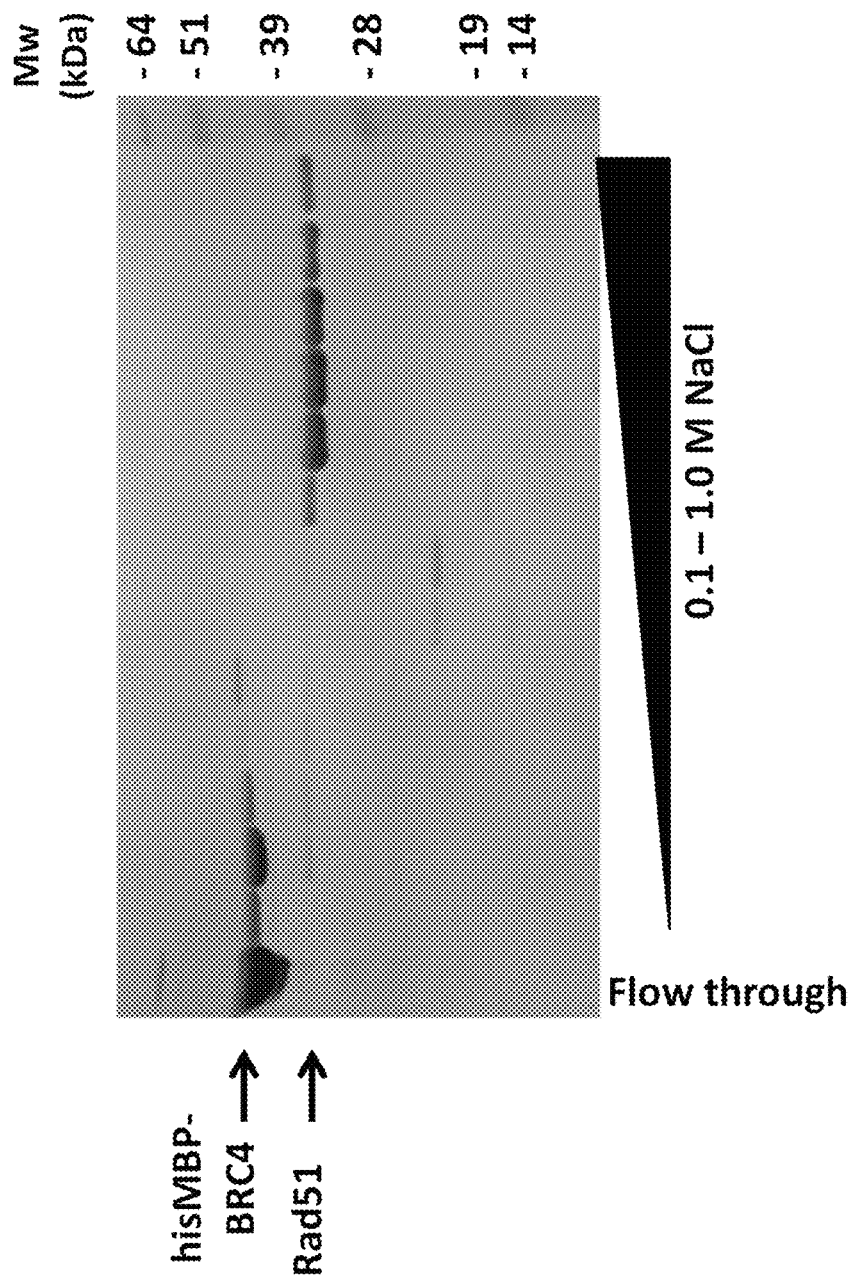
FIG. 6. Coomassie stained SDS-PAGE gel of various elution fractions obtained in RAD51 purification via heparin affinity shown in FIG. 5.

FIG. 6 is a Coomassie stained SDS-PAGE gel of various elution fractions obtained from the heparin affinity chromatography shown in FIG. 5. FIG. 6 shows that the 6Xhis-MBP-BRC4 fusion protein eluted early in the NaCl gradient, whereas the RAD51 protein bound eluted near 600 mM NaCl. Peak fractions containing the RAD51 protein may be pooled together.

The pooled RAD51 protein may be concentrated by any protein concentration means. For example, protein may be concentrated using centrifugal filters units with Molecular Weight Cut Off filters specific to the protein of interest. Protein may be concentrated using any ultrafiltration or depth filtration technique.

Figure 7:
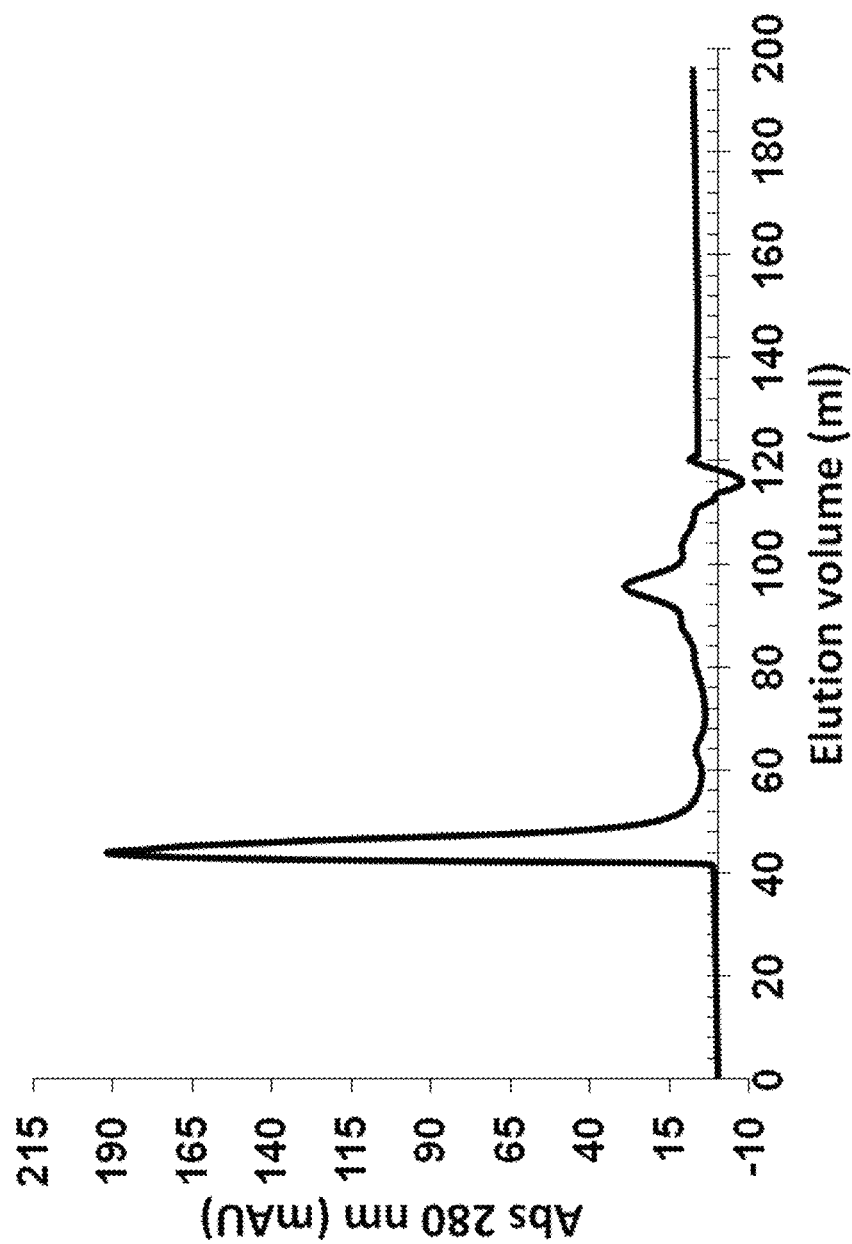
FIG. 7. Elution profile of RAD51 protein purification via a Superdex 200 size exclusion resin.

The pooled fractions containing the purified RAD51 protein may then be applied onto a size exclusion resin (also known referred to as a gel filtration resin), for example, Superdex 200 resin. The size exclusion resin may be equilibrated with an equilibration buffer, such as 20 mM Tris pH 8.0, 300 mM NaCl prior to injection of the RAD 51 sample. FIG. 7 shows an elution profile of RAD51 applied to a Superdex size exclusion column; oligomeric RAD51 elutes from the column largely in the void volume. Any other size exclusion/gel filtration resin or resin used to separate proteins based on size and or shape may be used.

Figure 8:
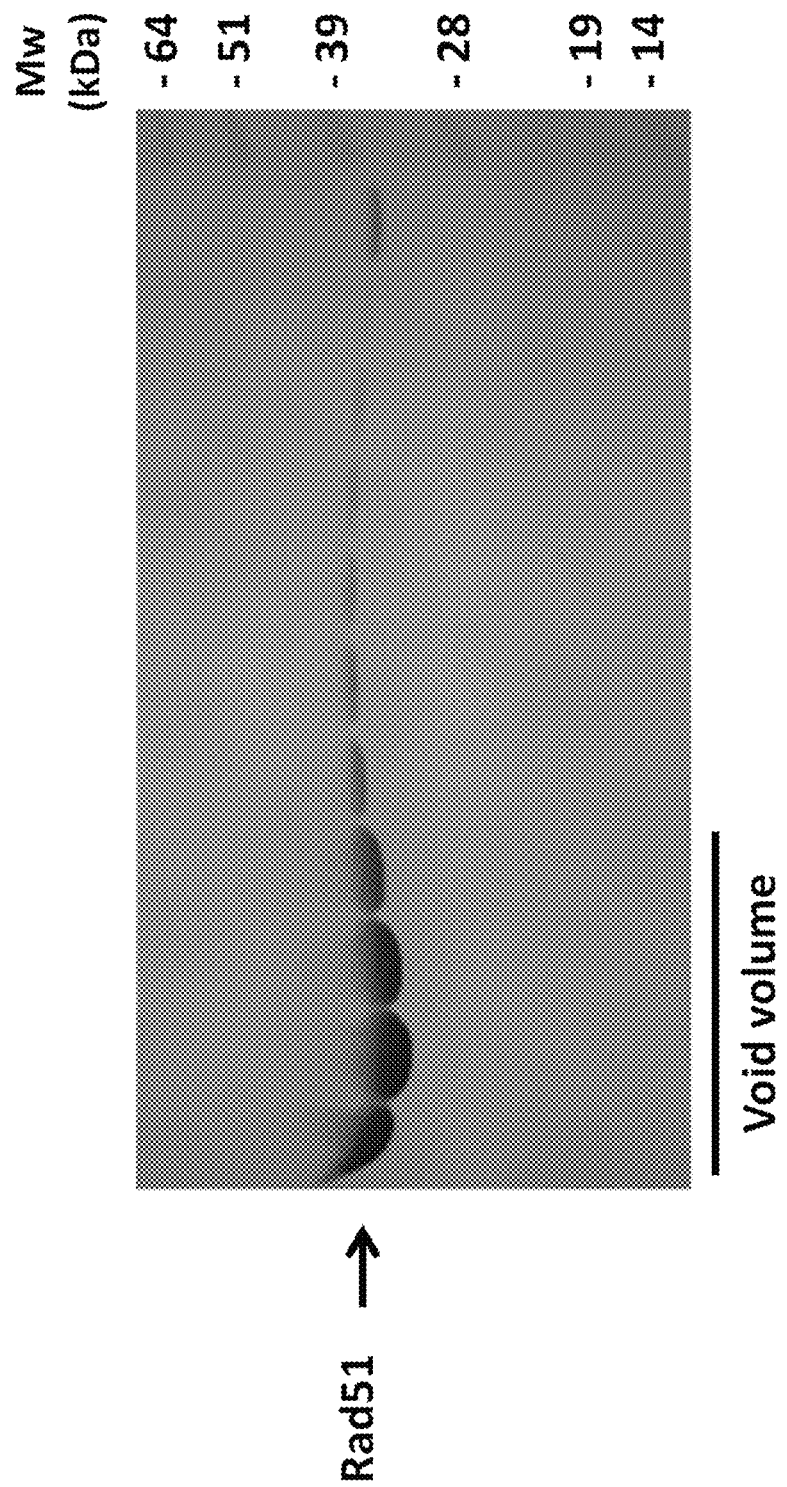
FIG. 8. Coomassie stained SDS-PAGE gel of various elution fractions obtained in RAD51 purification via the Superdex 200 size exclusion resin in FIG. 7.

FIG. 8 is a Coomassie stained SDS-PAGE gel of various elution fractions obtained from the Superdex 200 size exclusion chromatography shown in FIG. 7. FIG. 8 shows that the RAD51 protein eluted predominantly in the void volume. Peak fractions containing the RAD51 protein may be pooled together.

Any buffer additive such as DTT (for example 1 mM final DTT concentration) may be added to the purified RAD51 sample. The pooled RAD51 protein may be concentrated and snap frozen in liquid N$_2$ for storage in a freezer, for example at −80° C. The pooled RAD51 protein may also be stabilized in a buffer for storage at room temperature, or lyophilized, or prepared for storage in any storage means known by one of ordinary skill in the art.

Figure 9:
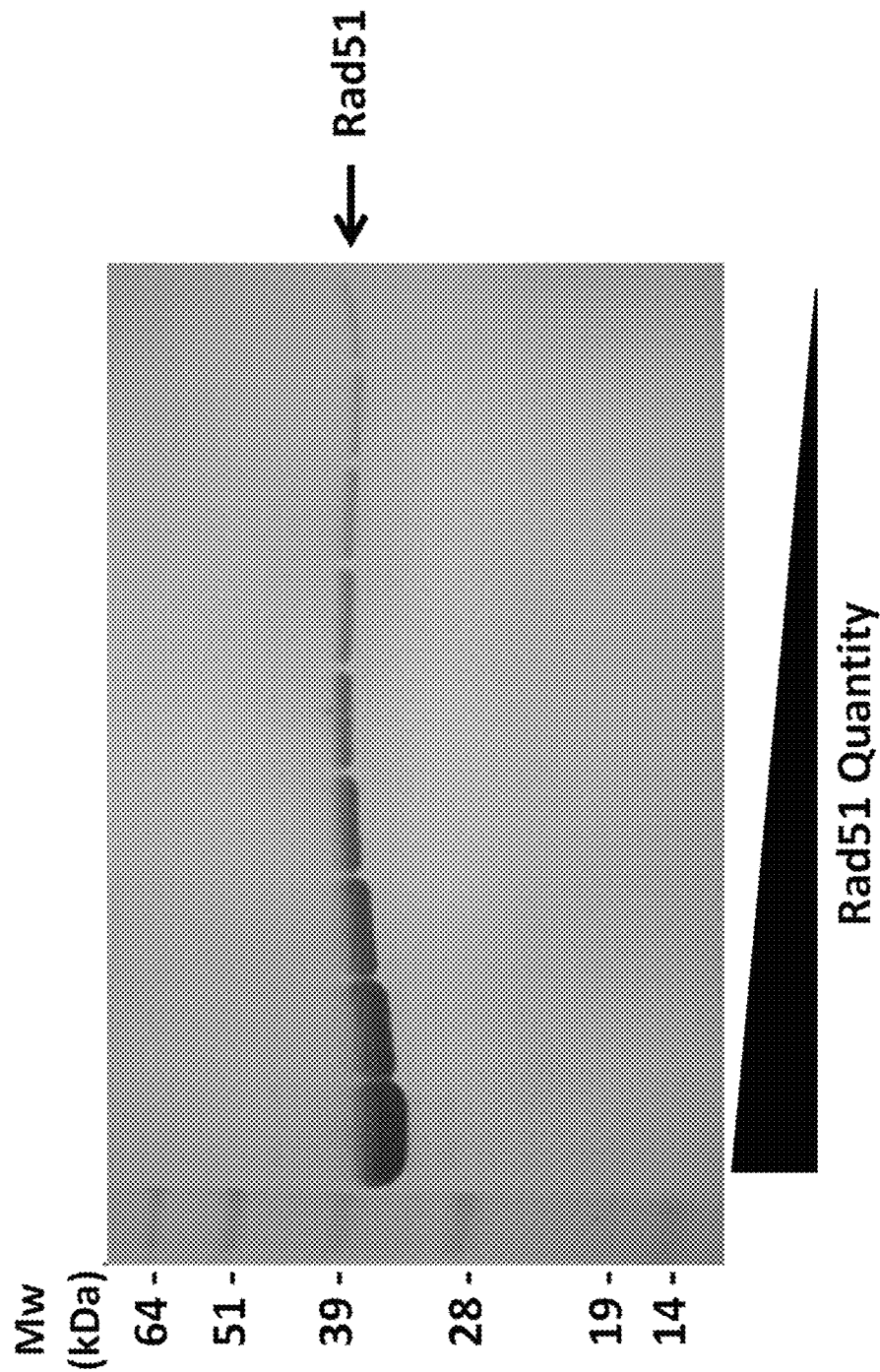
FIG. 9. Coomassie stained SDS-PAGE of final purified RAD51 protein loaded in decreasing concentration from left to right.

FIG. 9 is a Coomassie stained SDS-PAGE gel of the final RAD51 protein product loaded in decreasing concentration. Results show a highly pure RAD51 protein.

The purification of RAD51 may be performed in any sequential combination of chromatography resins as described herein as known by one with ordinary skill in the art.

(iv) Purification of DMC1

All recombinant protein expression may be initiated from fresh overnight transformation of *E. coli* strain BL21, harboring the pRARE plasmid (chloramphenicol resistance), with the co-overexpression plasmid, such as the pRSF-Duet1-6Xhis-MBP-BRC4-G85RAD51 co DMC1 vector. An entire plate of freshly formed colonies is then scraped and used to seed a starter culture (Turbo Broth culture medium—Athena Enzyme Systems) supplemented with the appropriate antibiotic (routinely both kanamycin and chloramphenicol). A starter culture of may be prepared in an orbital shaker (shaking at an rpm of 180-200 rpm at 37° C.) that is grown to reach an OD$_{600}$≥1.0. A volume of the dense starter culture is then used to seed each liter of culture grown (for example 1L Turbo broth, in 2 L dimpled shake flasks, 8 L total) and allowed to reach OD$_{600}$≥1.0. Any volume of culture may be grown for overexpression. At OD$_{600}$≥~1, over-expression is induced by addition of IPTG, for example a concentration of 200 μM IPTG may be used. The recombinant proteins, such as 6XHis-MBP-BRC4-G85RAD1 fusion protein and the DMC1 protein are overexpressed upon the addition of IPTG. After induction the cell cultures may be grown for an appropriate amount of time to overexpress protein from the induced promoter. For example, cells may be grown for 3 hours at 37° C. while shaking or for 15 hours or overnight at 15° C. while shaking.

Once the 6XHis-MBP-BRC4-G85RAD1 fusion protein and the DMC1 protein are overexpressed, the cells are harvested. Harvesting of cell cultures may be performed by centrifugation, for example centrifugation at 4,200 rpm for 30 minutes at 4° C. The cell pellet may then be lysed in a stabilizing buffer or in cell lysis buffer. An example of cell lysis buffer is 20 mM Tris pH 8.0, 500 mM NaCl, 20 mM imidazole. Additives such as carbohydrates, lysozyme, detergents, reducing agents, or protease inhibitors (such as SIGMAfast™ EDTA-free Protease inhibitor tablets) may be added to the lysis buffer. Cell lysis may be performed using any cell lysis method known by one of ordinary skill in the art. For example, cells may be lysed via a lysis buffer, French Press, sonication, high pressure homogenization (for example an Avestin EmulsiFlex-C5 high pressure homogenizer), jet milling, bead milling, or freeze thaw cycles. In a preferred embodiment, cells are lysed by flash freezing in liquid N$_2$.

The cell lysate may be filtered or centrifuged to separate insoluble cell debris and precipitated debris from soluble protein such as the 6XHis-MBP-BRC4-G85RAD1 fusion protein and the DMC1 protein. In a preferred embodiment, the cell lysate may be centrifuged at 30,000 g for 1 hour at 4° C. After centrifugation, the supernatant may be passed through a filter, for example a 5 μm filter, to remove any remaining insoluble particles in preparation for column chromatography. After centrifugation and/or filtration, the soluble protein (referred to as the cell extract), is applied to a chromatography resin, for example a resin specific to the affinity tag that is fused to the BRC4 repeat motif.

The co-overexpressed 6XHis-MBP-BRC4-G85RAD1 fusion protein and the DMC1 protein interact and form protein-protein bonds with each other as shown in FIG. 11, permitting for their co-purification. For example, purification of the 6XHis-MBP-BRC4-G85RAD1 fusion protein and DMC1 protein from cell extract may be achieved by applying the cell extract to a resin containing immobilized NTA resin, such as Sepharose HP Hi-Trap™ resin (GE Healthcare Life Sciences), charged with $Ni^{2+}$. A purification system, such as an ÄKTA Protein Purification System (GE Healthcare Life Sciences), may be used for protein purification. The 6X histidine tag in the 6XHis-MBP-BRC4-G85RAD1 fusion protein binds to the $Ni^{2+}$-NTA resin while concurrently the RAD51 F-X-X-A ATPase motif in G85RAD51 binds to the DMC1 protein. The bound proteins may be washed with a wash buffer, for example a wash buffer containing 20 mM Tris pH 8.0, 500 mM NaCl, 20 mM Imidazole. The 6XHis-MBP-BRC4-G85RAD1 fusion protein along with the DMC1 protein may then be eluted from the $Ni^{2+}$-NTA resin using increasing concentration of imidazole (not shown), wherein the mAU peak at 100% B is the elution of the 6XHis-MBP-BRC4-G85RAD1 fusion protein bound to the DMC1 protein. The elution buffer may be 20 mM Tris pH 8.0, 500 mM NaCl, 200 mM imidazole.

In one embodiment, the pooled fractions containing the DMC1 protein bound to the 6XHis-MBP-BRC4-G85RAD1 fusion protein may then be loaded onto an amylose resin that binds to MBP. The 6XHis-MBP-BRC4-G85RAD1 fusion protein (along with the associated DMC1 protein) binds to the amylose resin. The bound protein my then be washed with wash a wash buffer, for example 20 mM Tris pH 8.0, 500 mM NaCl. Bound protein may then be eluted with elution buffer, for example with 20 mM Tris, pH 8.0, 500 mM NaCl, and 20 mM maltose.

Figure 12:
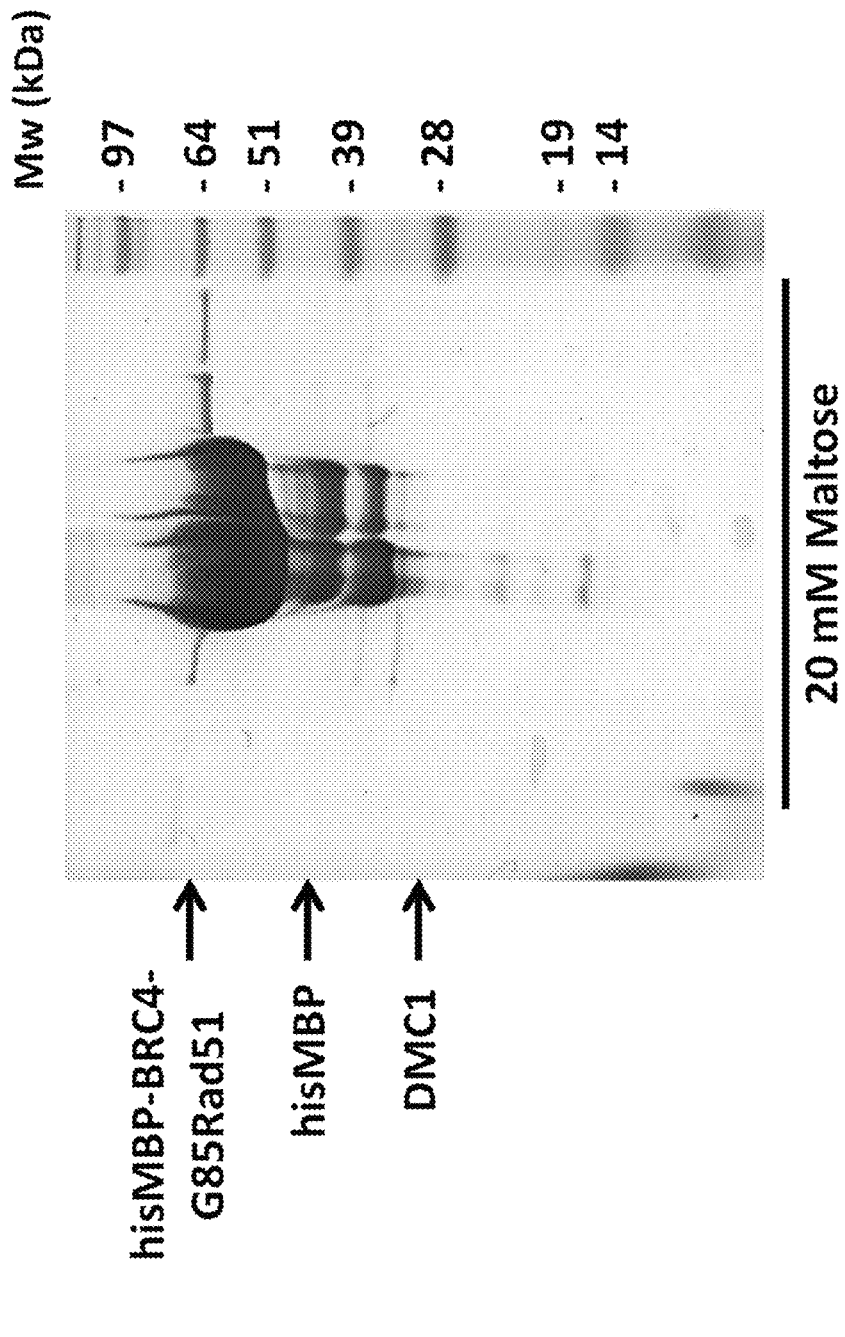
FIG. 12. Coomassie stained SDS-PAGE gel showing purification of DMC1 protein and 6Xhis-MBP-tagged-BRC4-G85RAD51 ATPase domain fusion protein via MBP-tag affinity using immobilized amylose.

FIG. 12 is a coomassie stained SDS-PAGE gel of various elution fractions of 6XHis-MBP-BRC4-G85RAD1 fusion protein and DMC1 protein obtained from the amylose resin chromatography. FIG. 12 shows that the DMC1 protein co-eluted with the 6XHis-MBP-BRC4-G85RAD1 fusion protein in 20 mM maltose. Peak fractions containing the DMC1 protein may be pooled together.

In another embodiment, if the fusion protein construct was designed with an alternative protein tag, for example a GST tag, then an alternative affinity resin may be used specific for the alternative tag, for example Glutathione Sepharose resin wherein glutathione would be used to elute bound tagged fusion protein along with proteins associated via protein-protein to the fusion tagged protein.

Following elution of the 6XHis-MBP-BRC4-G85RAD1 fusion protein and DMC1 protein from the $Ni^{2+}$-NTA affinity resin, the pooled fractions may be processed by exchanging the sample buffer into a low salt buffer, for example by overnight dialyzing the pooled fractions using a dialysis membrane (for example a 6,000-8000 MWCO dialysis membrane) at 4° C. The said low salt concentration buffer may be Tris pH 8.0, containing 50 mM NaCl.

In yet another embodiment, following elution of the 6XHis-MBP-BRC4-G85RAD1 fusion protein and DMC1 protein from the $Ni^{2+}$-NTA affinity resin, the pooled fractions may be diluted with a buffer, for example diluted 5-fold with 20 mM Tris pH 8.0, resulting in a sample with a NaCl concentration of near 100 mM.

The dialyzed protein sample in low salt buffer may then be applied to a chromatography resin containing an immobilized molecule that is known to generally mimic DNA molecules. One exemplary molecule is heparin which is known to one with ordinary skill in the art to efficiently bind to a variety of DNA binding proteins. For example, the dialyzed protein may be applied to a Heparin Sepharose HiTrap™ HF resin (GE Healthcare Life Science). The DMC1 protein has biding specificity to the heparin ligand and will bind to the heparin ligand along with the bound 6XHis-MBP-BRC4-G85RAD1 fusion protein. Increasing the NaCl concentration, for example from 0.1 to 1.5 M, will elute proteins bound to the heparin ligand. The heparin ligand with bound protein may be washed with a wash buffer, for example 20 mM Tris pH 8.0 and 200 mM, followed by elution with a linear 0.2M-0.7 M NaCl gradient as shown in FIG. 5. The 6XHis-MBP-BRC4-G85RAD1 fusion protein will elute early in the NaCl gradient, while DMC1 will elute near 600 mM NaCl as shown in heparin affinity chromatography elution profile FIG. 13.

Figure 13:
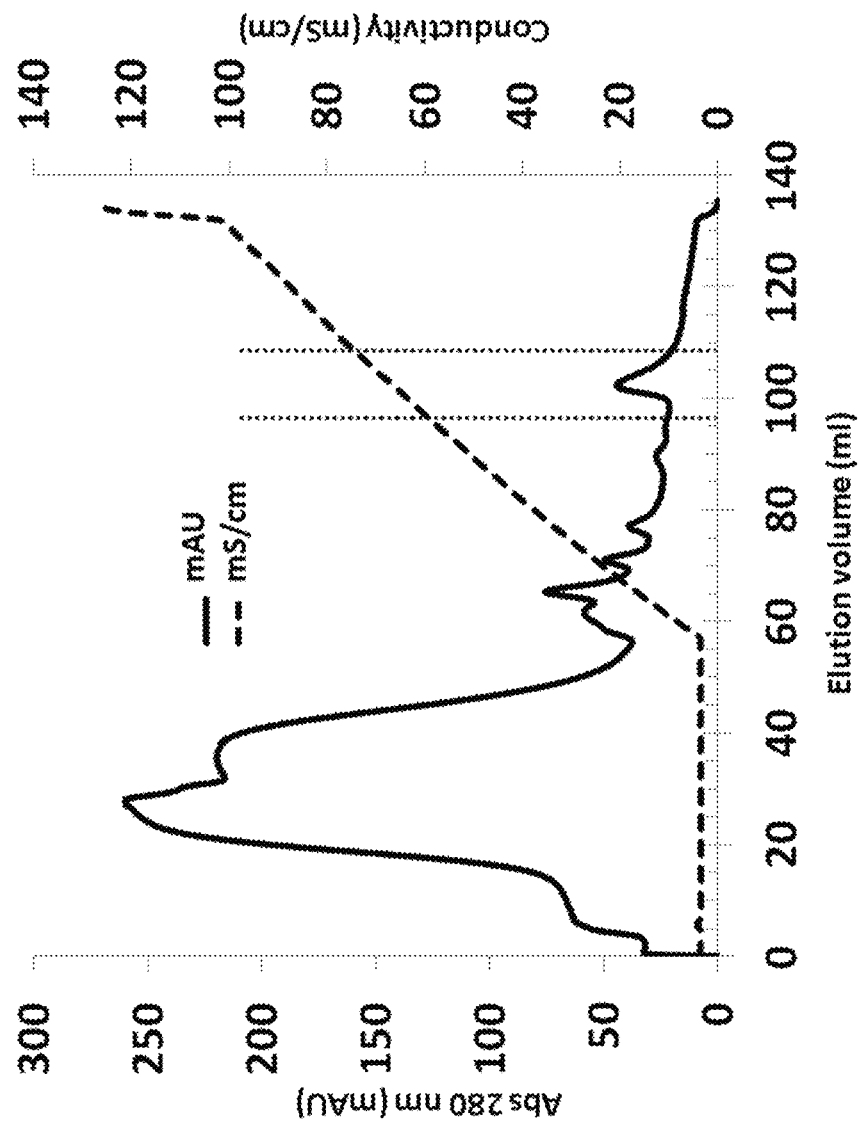
FIG. 13. Elution profile of DMC1 protein purification via affinity to heparin using an increasing NaCl concentration.
Figure 14:
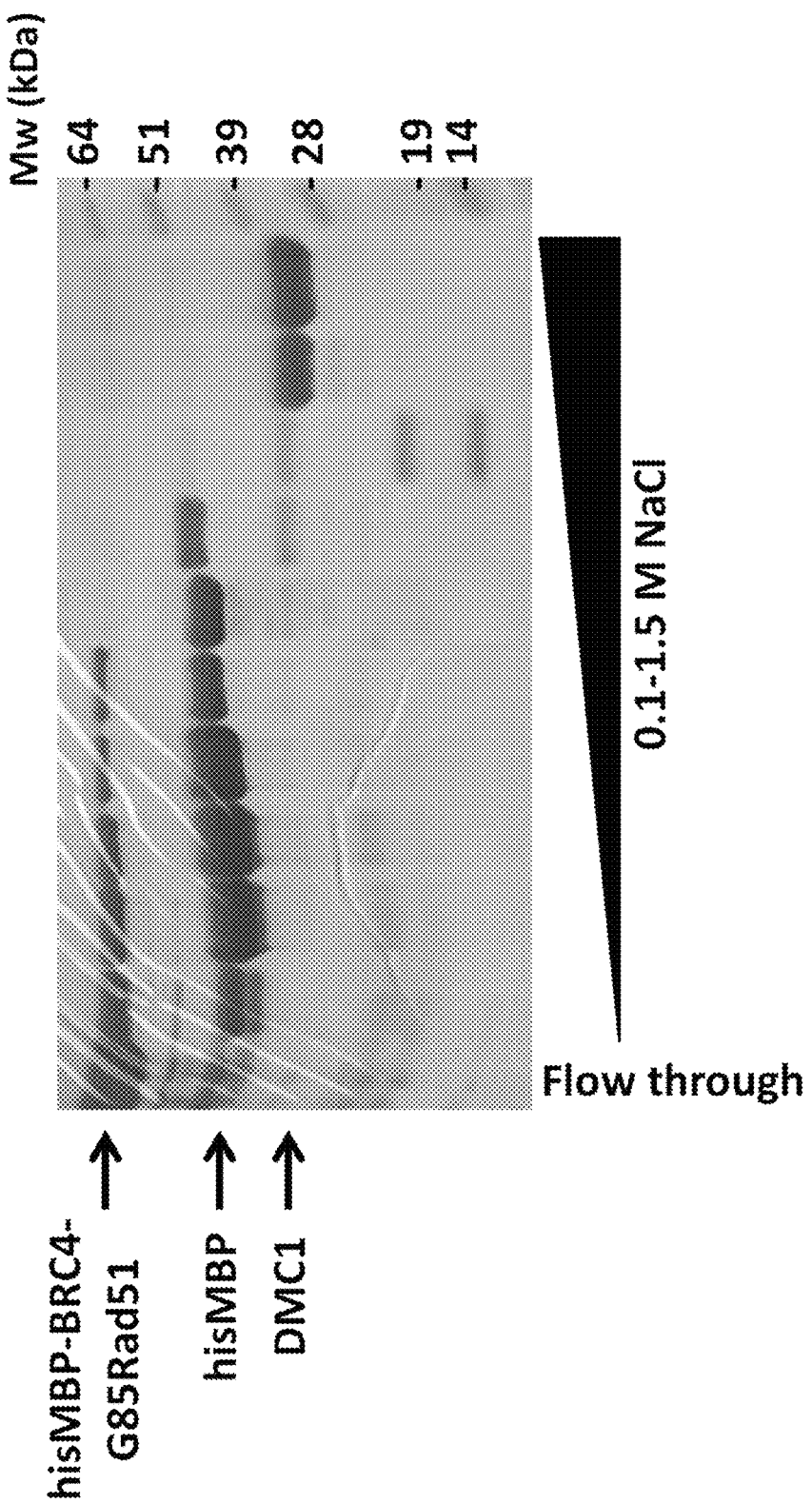
FIG. 14. Coomassie stained SDS-PAGE gel of various elution fractions obtained from DMC1 protein purification via affinity to heparin shown in FIG. 13.
Figure 15:
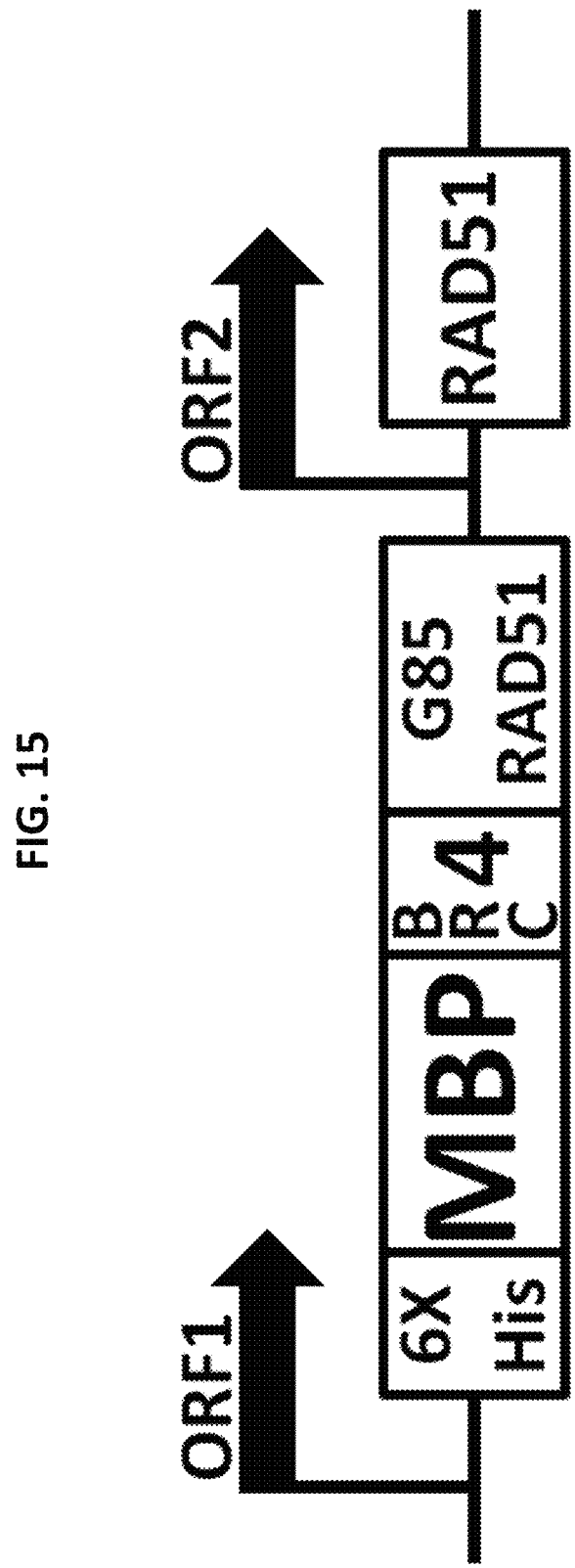
FIG. 15. Diagram representation of vector construct for co-overexpression of 6Xhis-MBP-tagged-BRC4-Rad51 ATPase domain fusion protein from ORF1 and RAD51 protein from ORF 2.
Figure 16A:
FIG. 16A. Representation of 6Xhis-MBP-tagged-BRC4-G85RAD51 and RAD51 proteins.
Figure 16B:
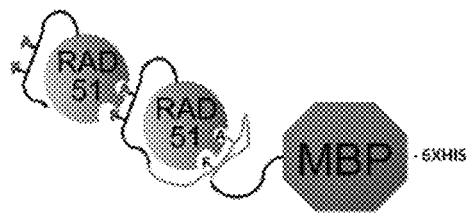
FIG. 16B. Representation of 6Xhis-MBP-tagged-BRC4-G85RAD51 fusion protein interacting with RAD51 protein.

FIG. 14 is a coomassie stained SDS-PAGE gel of various elution fractions obtained from the heparin affinity chromatography DMC1 purification shown in FIG. 13. FIG. 14 shows that the 6XHis-MBP-BRC4-G85RAD1 fusion protein eluted early in the NaCl gradient, whereas the bound DMC1 protein eluted near 600 mM NaCl. Peak fractions containing the DMC1 protein may be pooled together.

The pooled DMC1 protein may be concentrated by any protein concentration means. For example, protein may be concentrated using centrifugal filters units with Molecular Weight Cut Off filters specific to the protein of interest. Protein may be concentrated using any ultrafiltration or depth filtration technique.

The pooled fractions containing the purified DMC1 protein may then be applied onto a size exclusion resin (also known referred to as a gel filtration resin), for example, Superdex 200 resin. The size exclusion resin may be equilibrated with an equilibration buffer, such as 20 mM Tris pH 8.0, 300 mM NaCl prior to injection of the DMC1 sample. Any other size exclusion/gel filtration resin or resin used to separate proteins based on size and or shape may be used.

Any buffer additive such as DTT (for example 1 mM final DTT concentration) may be added to the purified DMC1 sample. The pooled DMC1 protein may be concentrated and snap frozen in liquid $N_2$ for storage in a freezer, for example at −80° C. The pooled DMC1 protein may also be stabilized in a buffer for storage at room temperature, or lyophilized, or prepared for storage in any storage means known by one of ordinary skill in the art.

Purification of DMC1 may be performed in any sequential combination of chromatography resins as described herein as known by one with ordinary skill in the art.

(v) Uses

The present invention may be used to purify recombinase proteins which have an affinity for the RAD51 ATPase F-X-X-A repeat motif or for the BRC4 F-X-X-A repeat motif. The purified recombinase may be used in reagent, diagnostic, and therapeutic applications.

Such use may be employed in, but is not limited to, chromatography, microtiter plates, Western blots, ELISA, or magnetic bead based isolation.

Alternatively, the purified recombinase protein may be used functionally to the action of target molecules. The target molecule may have an activity which the purified recombinase protein enhances or inhibits.

While the specification describes particular embodiments of the present invention, those of ordinary skill in the art can devise variations of the present invention without departing from the inventive concept.

REFERENCE TO A SEQUENCE LISTING SUBMITTED ON COMPUTER

The content of the ASCII text file of the sequence listing named "Recombinase_CIP_30735_seq.txt" is 71,735 bytes in size, with a created date of Tuesday, Jun. 4, 2020, and electronically submitted via EFS-Web herewith the application, is incorporated herein by reference in its entirety.

What is claimed is:

1. A method of purifying a recombinase protein, comprising:
   a. inserting at least one expression vector into a single host cell, wherein said at least one expression vector comprises at least a first coding sequence and a second coding sequence, and the first coding sequence and the second coding sequence is under the control of at least one promoter, wherein the first coding sequence encodes for a tagged fusion protein comprising a mutated BRCA2 protein motif, wherein the mutated BRCA2 protein motif comprises at least one BRC repeat comprising at least one substitution in an F-X-X-A motif as shown in the amino acid sequence 409-412 in SEQ ID NO: 22, wherein the substitution comprises a non-polar amino acid or hydrophobic amino acid in place of the F position of the F-X-X-A motif, or a non-polar amino acid, hydrophobic amino acid, or serine in place of the A position of the F-X-X-A motif, and the second coding sequence encodes for a recombinase protein that has a binding affinity to the mutated BRCA2 protein motif of the first coding sequence;
   b. expressing the tagged fusion protein and the recombinase protein from under the control of the at least one promoter in the host cell; and
   c. isolating the recombinase protein from the host cell using a protein purification procedure that comprises of procedures that select for the tagged fusion protein.

2. The method of claim 1, wherein the mutated BRC repeat comprises an φ-X-X-A motif where φ is a hydrophobic amino acid.

3. The method of claim 1, wherein the mutated BRC repeat comprises φ-X-X-G motif where φ is a hydrophobic amino acid.

4. The method of claim 1, wherein the mutated BRC repeat comprises an F-X-X-φ motif where φ is a hydrophobic amino acid.

5. The method of claim 1, wherein the mutated BRC repeat comprises an F-X-X-U motif as shown by substituting an α-amino butyric (U) for the alanine in the amino acid sequence 409-412 in SEQ ID NO: 22.

6. The method of claim 1 wherein said at least one protein tag comprises a 6Xhis tag, an MBP tag, a GST tag, a FLAG tag, a myc tag, or a Strep tag or any combination of protein tags.

7. The method of claim 6, wherein the first coding sequence further comprises a 6Xhis tag and an MBP tag and the mutated BRC4 protein motif.

8. The method of claim 1, wherein the second coding sequence encodes for human RAD51 recombinase.

9. The method of claim 1 wherein the protein purification procedure comprises a first ligand that binds to the tagged fusion protein and because the recombinase is bound to the tagged fusion protein, the first ligand is used to isolate both the tagged fusion protein and the recombinase protein together.

10. The method of claim 9 wherein the tagged fusion protein and the recombinase protein are separated from each other using a second ligand, wherein the second ligand binds to the recombinase protein in a manner that promotes dissociation between the tagged fusion protein and the recombinase protein.

11. The method of claim 10 wherein the recombinase protein is further purified using a method that selects proteins based on their size.

12. The method of claim 9 wherein the first ligand comprises a metal chelator and/or amylase ligand.

13. The method of claim 10 wherein the second ligand is heparin.

14. The method of claim 1, wherein the tagged fusion protein comprises at least one protein tag.

* * * * *

SEQUENCE LISTING

<160> NUMBER OF SEQ ID NOS: 32

<210> SEQ ID NO 1
<211> LENGTH: 32
<212> TYPE: DNA
<213> ORGANISM: Artificial Sequence
<220> FEATURE:
<223> OTHER INFORMATION: Synthetic Construct

<400> SEQUENCE: 1
atatatacat atggcaatgc agatgcagct tg            32

<210> SEQ ID NO 2
<211> LENGTH: 38
<212> TYPE: DNA
<213> ORGANISM: Artificial Sequence
<220> FEATURE:
<223> OTHER INFORMATION: Synthetic Construct

<400> SEQUENCE: 2
tatatcctag gttattagtc tttggcatct cccactcc     38

<210> SEQ ID NO 3
<211> LENGTH: 32
<212> TYPE: DNA
<213> ORGANISM: Artificial Sequence
<220> FEATURE:
<223> OTHER INFORMATION: Synthetic Construct

<400> SEQUENCE: 3
agttgcccat atgaaggagg atcaagttgt gg            32

<210> SEQ ID NO 4
<211> LENGTH: 39
<212> TYPE: DNA
<213> ORGANISM: Artificial Sequence
<220> FEATURE:
<223> OTHER INFORMATION: Synthetic Construct

<400> SEQUENCE: 4
gtacaaccta ggttattact ccttcgcatc cccaattcc    39

<210> SEQ ID NO 5
<211> LENGTH: 56
<212> TYPE: DNA
<213> ORGANISM: Artificial Sequence
<220> FEATURE:
<223> OTHER INFORMATION: Synthetic Construct

<400> SEQUENCE: 5
attgggcgcg cctggaaaac ctgtattttc agggatccaa agaaccgacc ctgctg    56

<210> SEQ ID NO 6
<211> LENGTH: 36
<212> TYPE: DNA
<213> ORGANISM: Artificial Sequence
<220> FEATURE:
<223> OTHER INFORMATION: Synthetic Construct

<400> SEQUENCE: 6
agctgcggcc gcttattagt cgaacaggtt tttaac        36

<210> SEQ ID NO 7
<211> LENGTH: 53
<212> TYPE: DNA
<213> ORGANISM: Artificial Sequence
<220> FEATURE:
<223> OTHER INFORMATION: Synthetic Construct

<400> SEQUENCE: 7
actgcaactg aattccacca acgtcgctca gagatcatac agattactac tgg                53

<210> SEQ ID NO 8
<211> LENGTH: 39
<212> TYPE: DNA
<213> ORGANISM: Artificial Sequence
<220> FEATURE:
<223> OTHER INFORMATION: Synthetic Construct

<400> SEQUENCE: 8
agctgcggcc gcttatcagt ctttggcatc tcccactcc                                39

<210> SEQ ID NO 9
<211> LENGTH: 29
<212> TYPE: DNA
<213> ORGANISM: Artificial Sequence
<220> FEATURE:
<223> OTHER INFORMATION: Synthetic Construct

<400> SEQUENCE: 9
gaataggatc caaagaaccg accctgctg                                           29

<210> SEQ ID NO 10
<211> LENGTH: 70
<212> TYPE: DNA
<213> ORGANISM: Artificial Sequence
<220> FEATURE:
<223> OTHER INFORMATION: Synthetic Construct

<400> SEQUENCE: 10
ggaattcagt tgcagtggta aagccagagc cagtgctgcc agtgctgcca gtgtcgaaca         60
ggttttaac                                                                70

<210> SEQ ID NO 11
<211> LENGTH: 39
<212> TYPE: DNA
<213> ORGANISM: Artificial Sequence
<220> FEATURE:
<223> OTHER INFORMATION: Synthetic Construct

<400> SEQUENCE: 11
agctgcggcc gcttatcagt ctttggcatc tcccactcc                                39

<210> SEQ ID NO 12
<211> LENGTH: 1017
<212> TYPE: DNA
<213> ORGANISM: Homo sapiens

<400> SEQUENCE: 12
atggcaatgc agatgcagct tgaagcaaat gcagatactt cagtggaaga agaaagcttt         60
ggcccacaac ccatttcacg gttagagcag tgtggcataa atgccaacga tgtgaagaaa        120
ttggaagaag ctggattcca tactgtggag gctgttgcct atgcgccaaa gaaggagcta        180
ataaatatta agggaattag tgaagccaaa gctgataaaa ttctggctga ggcagctaaa        240
ttagttccaa tgggtttcac cactgcaact gaattccacc aaaggcggtc agagatcata        300
cagattacta ctggctccaa agagcttgac aaactacttc aaggtggaat tgagactgga        360
tctatcacag aaatgtttgg agaattccga actgggaaga cccagatctg tcatacgcta        420

```
gctgtcacct gccagcttcc cattgaccgg ggtggaggtg aaggaaaggc catgtacatt      480
gacactgagg gtacctttag gccagaacgg ctgctggcag tggctgagag gtatggtctc      540
tctggcagtg atgtcctgga taatgtagcc tatgctcgcg cgttcaacac agaccaccag      600
acccagctcc tttatcaagc atcagccatg atggtagaat ctaggtatgc actgcttatt      660
gtagacagtg ccaccgccct ttacagaaca gactactcgg gtcgaggtga gctttcagcc      720
aggcagatgc acttggccag gtttctgcgg atgcttctgc gactcgctga tgagtttggt      780
gtagcagtgg taatcactaa tcaggtggta gctcaagtgg atggagcagc gatgtttgct      840
gctgatccca aaaacctat tggaggaaat atcatcgccc atgcatcaac aaccagattg      900
tatctgagga aaggaagagg ggaaaccaga atctgcaaaa tctacgactc tccctgtctt      960
cctgaagctg aagctatgtt cgccattaat gcagatggag tgggagatgc caaagac      1017
```

<210> SEQ ID NO 13
<211> LENGTH: 93
<212> TYPE: DNA
<213> ORGANISM: Homo sapiens

<400> SEQUENCE: 13

```
aaagaaccga ccctgctggg tttccacacc gcttccggta aaaagttaa aatcgctaaa       60 gaatccctgg acaaagttaa aaacctgttc gac                                   93
```

<210> SEQ ID NO 14
<211> LENGTH: 765
<212> TYPE: DNA
<213> ORGANISM: Artificial Sequence
<220> FEATURE:
<223> OTHER INFORMATION: Synthetic Construct

<400> SEQUENCE: 14

```
ggtttcacca ctgcaactga attccaccaa aggcggtcag agatcataca gattactact       60
ggctccaaag agcttgacaa actacttcaa ggtggaattg agactggatc tatcacagaa      120
atgtttggag aattccgaac tgggaagacc cagatctgtc atacgctagc tgtcacctgc      180
cagcttccca ttgaccgggg tggaggtgaa ggaaaggcca tgtacattga cactgagggt      240
acctttaggc cagaacggct gctggcagtg gctgagaggt atggtctctc tggcagtgat      300
gtcctggata tgtagccta tgctcgcgcg ttcaacacag accaccagac ccagctcctt      360
tatcaagcat cagccatgat ggtagaatct aggtatgcac tgcttattgt agacagtgcc      420
accgcccttt acagaacaga ctactcgggt cgaggtgagc tttcagccag gcagatgcac      480
ttggccaggt ttctgcggat gcttctgcga ctcgctgatg agtttggtgt agcagtggta      540
atcactaatc aggtggtagc tcaagtggat ggagcagcga tgtttgctgc tgatcccaaa      600
aaacctattg gaggaaatat catcgcccat gcatcaacaa ccagattgta tctgaggaaa      660
ggaagagggg aaaccagaat ctgcaaaatc tacgactctc cctgtcttcc tgaagctgaa      720
gctatgttcg ccattaatgc agatggagtg ggagatgcca aagac                      765
```

<210> SEQ ID NO 15
<211> LENGTH: 1020
<212> TYPE: DNA
<213> ORGANISM: Homo sapiens

<400> SEQUENCE: 15

```
atgaaggagg atcaagttgt ggcggaagaa ccaggattcc aagatgaaga ggaatctttg       60
tttcaagata ttgacctgtt acagaaacat ggaattaacg tggctgacat taagaaactg      120
```

```
aaatcagtag gaatctgtac catcaaaggt atacagatga caacaagaag agctctatgc    180
aatgtcaaag gactctcaga agccaaagta gacaagatta agaggcagc gaacaaacta     240 attgaaccag gattcttgac tgcatttgag tatagtgaaa agaggaaaat ggttttccat    300
atcaccaccg ggagccagga atttgataag ttactaggag gtggaattga agtatggca    360 attacagaag cttttggaga atttcgtact ggaaaaaccc agctttctca taccctctgt    420
gtgacagctc aacttccagg agctggtggc tacccaggag aaagattat cttcattgat     480 acagaaaata ctttccgtcc agatcgcctt agggacattg ctgatcgctt taatgtagac    540
catgatgcag tactggacaa cgtactttat gcacgtgcat atactagtga acatcagatg    600
gagctacttg attatgtagc agcaaagttc catgaagaag ctggcatctt caagctattg    660
attatcgatt caataatggc actttttcga gtggatttca gtggccgtgg ggagttggcc    720
gaacggcagc aaaaattggc ccagatgttg tcacgactcc aaaaaatctc agaagaatat    780
aacgtggctg ttttttgtgac caatcaaatg actgccgatc caggagcaac tatgaccttt    840
caggcagatc ccaaaaaacc cattggggga cacattctgg ctcatgcttc aacaacaaga    900
ataagcttgc gaaagggaag aggagagctc agaattgcca gatttatga cagtcctgag     960 atgcctgaaa atgaagccac cttcgcaata actgctggag gaattgggga tgcgaaggag   1020

<210> SEQ ID NO 16
<211> LENGTH: 1296
<212> TYPE: DNA
<213> ORGANISM: Artificial Sequence
<220> FEATURE:
<223> OTHER INFORMATION: Synthetic Construct

<400> SEQUENCE: 16
atggacacca ttcatcacca tcaccatcac aacactagta tgaaaatcga agaaggtaaa     60
ctggtaatct ggattaacgg cgataaaggc tataacggtc tcgctgaagt cggtaagaaa    120
ttcgagaaag ataccggaat taaagtcacc gttgagcatc cggataaact ggaagagaaa    180
ttcccacagg ttgcggcaac tggcgatggc cctgacatta tcttctgggc acacgaccgc    240
tttggtggct acgctcaatc tggcctgttg gctgaaatca ccccgacaa agcgttccag      300 gacaagctgt atccgtttac ctgggatgcc gtacgttaca acggcaagct gattgcttac    360
ccgatcgctg ttgaagcgtt atcgctgatt tataacaaa atctgctgcc gaacccgcca      420
aaaacctggg aagagatccc ggcgctggat aaagaactga agcgaaagg taagagcgcg     480 ctgatgttca acctgcaaga accgtacttc acctggccgc tgattgctgc tgacgggggt    540
tatgcgttca gtatgaaaa cggcaagtac gacattaaag acgtgggcgt ggataacgct    600
ggcgcgaaag cggtctgac cttcctggtt gacctgatta aaacaaaaca catgaatgca    660
gacaccgatt actccatcgc agaagctgcc tttaataaag gcgaaacagc gatgaccatc    720 aacgcccgt gggcatggtc caacatcgac accagcaaag tgaattatgg tgtaacggta    780
ctgccgacct tcaagggtca accatccaaa ccgttcgttg gcgtgctgag cgcaggtatt    840
gacgccgcca gtccgaacaa agagctggca aaagagttcc tcgaaaacta tctgctgact    900
gatgaaggtc tggaagcggt taataaagac aaaccgctgg gtgccgtagc gctgaagtct    960
tacgaggaag agttggcgaa agatccacgt attgccgcca aatggaaaa cgcccagaaa    1020 ggtgaaatca tgccgaacat cccgcagatg tccgcttctc tggtatgccgt gcgtactgcg    1080 gtgatcaacg ccgccagcgg tcgtcagact gtcgatgaag ccctgaaaga cgcgcagact    1140
```

```
aattcgagct cgactagtgg atctggtggg gcgcgcctgg aaaacctgta ttttcaggga    1200
tccaaagaac cgaccctgct gggttttccac accgcttccg gtaaaaaagt taaaatcgct   1260
aaagaatccc tggacaaagt taaaaacctg ttcgac                              1296
```

<210> SEQ ID NO 17
<211> LENGTH: 2088
<212> TYPE: DNA
<213> ORGANISM: Artificial Sequence
<220> FEATURE:
<223> OTHER INFORMATION: Synthetic Construct

<400> SEQUENCE: 17

```
atggacacca ttcatcacca tcaccatcac aacactagta tgaaaatcga agaaggtaaa      60
ctggtaatct ggattaacgg cgataaaggc tataacggtc tcgctgaagt cggtaagaaa    120
ttcgagaaag ataccggaat taaagtcacc gttgagcatc cggataaact ggaagagaaa    180
ttcccacagg ttgcggcaac tggcgatggc cctgacatta tcttctgggc acacgaccgc    240
tttggtggct acgctcaatc tggcctgttg gctgaaatca ccccggacaa agcgttccag    300
gacaagctgt atccgtttac ctgggatgcc gtacgttaca acggcaagct gattgcttac    360
ccgatcgctg ttgaagcgtt atcgctgatt tataacaaaa tctgctgcc gaacccgcca     420 aaaacctggg aagagatccc ggcgctggat aaagaactga agcgaaagg taagagcgcg     480 ctgatgttca acctgcaaga accgtacttc acctggccgc tgattgctgc tgacgggggt    540
tatgcgttca gtatgaaaaa cggcaagtac gacattaaag acgtgggcgt ggataacgct    600
ggcgcgaaag cgggtctgac cttcctggtt gacctgatta aaacaaaca catgaatgca     660 gacaccgatt actccatcgc agaagctgcc tttaataaag gcgaaacagc gatgaccatc    720
aacggcccgt gggcatggtc caacatcgac accagcaaag tgaattatgg tgtaacggta    780
ctgccgacct tcaagggtca accatccaaa ccgttcgttg gcgtgctgag cgcaggtatt    840
gacgccgcca gtccgaacaa agagctggca aaagagttcc tcgaaaacta tctgctgact    900
gatgaaggtc tggaagcggt taataaagac aaaccgctgg gtgccgtagc gctgaagtct    960
tacgaggaag agttggcgaa agatccacgt attgccgcca aatggaaaaa cgcccagaaa   1020
ggtgaaatca tgccgaacat cccgcagatg tccgcttttct ggtatgccgt gcgtactgcg  1080
gtgatcaacg ccgccagcgg tcgtcagact gtcgatgaag ccctgaaaga cgcgcagact  1140
aattcgagct cgactagtgg atctggtggg gcgcgcctgg aaaacctgta ttttcaggga    1200
tccaaagaac cgaccctgct gggttttccac accgcttccg gtaaaaaagt taaaatcgct   1260
aaagaatccc tggacaaagt taaaaacctg ttcgacactg gcagcactgg cagcactggc  1320
tctggtttca ccactgcaac tgaattccac caaaggcggt cagagatcat acagattact  1380
actggctcca aagagcttga caaactactt caaggtggaa ttgagactgg atctatcaca  1440
gaaatgtttg agaattccg aactgggaag acccagatct gtcatacgct agctgtcacc  1500
tgccagcttc ccattgaccg gggtggaggt gaaggaaagg ccatgtacat tgacactgag  1560 ggtacctta ggccagaacg gctgctggca gtggctgaga ggtatggtct ctctggcagt    1620
gatgtcctgg ataatgtagc ctatgctcgc gcgttcaaca cagaccacca gacccagctc   1680
ctttatcaag catcagccat gatggtagaa tctaggtatg cactgcttat tgtagacagt   1740
gccaccgccc tttacagaac agactactcg ggtcgaggtg agctttcagc caggcagatg   1800
cacttggcca ggtttctgcg gatgcttctg cgactcgctg atgagtttgg tgtagcagtg   1860
gtaatcacta atcaggtggt agctcaagtg gatggagcag cgatgtttgc tgctgatccc   1920
```

-continued

```
aaaaaaccta ttggaggaaa tatcatcgcc catgcatcaa caaccagatt gtatctgagg    1980
aaaggaagag gggaaaccag aatctgcaaa atctacgact ctccctgtct tcctgaagct    2040
gaagctatgt tcgccattaa tgcagatgga gtgggagatg ccaaagac                 2088
```

<210> SEQ ID NO 18
<211> LENGTH: 339
<212> TYPE: PRT
<213> ORGANISM: Homo sapiens

<400> SEQUENCE: 18

```
Met Ala Met Gln Met Gln Leu Glu Ala Asn Ala Asp Thr Ser Val Glu
1               5                   10                  15

Glu Glu Ser Phe Gly Pro Gln Pro Ile Ser Arg Leu Glu Gln Cys Gly
            20                  25                  30

Ile Asn Ala Asn Asp Val Lys Lys Leu Glu Glu Ala Gly Phe His Thr
        35                  40                  45

Val Glu Ala Val Ala Tyr Ala Pro Lys Lys Glu Leu Ile Asn Ile Lys
    50                  55                  60

Gly Ile Ser Glu Ala Lys Ala Asp Lys Ile Leu Ala Glu Ala Ala Lys
65                  70                  75                  80

Leu Val Pro Met Gly Phe Thr Thr Ala Thr Glu Phe His Gln Arg Arg
                85                  90                  95

Ser Glu Ile Ile Gln Ile Thr Thr Gly Ser Lys Glu Leu Asp Lys Leu
            100                 105                 110

Leu Gln Gly Gly Ile Glu Thr Gly Ser Ile Thr Glu Met Phe Gly Glu
        115                 120                 125

Phe Arg Thr Gly Lys Thr Gln Ile Cys His Thr Leu Ala Val Thr Cys
    130                 135                 140

Gln Leu Pro Ile Asp Arg Gly Gly Gly Glu Gly Lys Ala Met Tyr Ile
145                 150                 155                 160

Asp Thr Glu Gly Thr Phe Arg Pro Glu Arg Leu Leu Ala Val Ala Glu
                165                 170                 175

Arg Tyr Gly Leu Ser Gly Ser Asp Val Leu Asp Asn Val Ala Tyr Ala
            180                 185                 190

Arg Ala Phe Asn Thr Asp His Gln Thr Gln Leu Leu Tyr Gln Ala Ser
        195                 200                 205

Ala Met Met Val Glu Ser Arg Tyr Ala Leu Leu Ile Val Asp Ser Ala
    210                 215                 220

Thr Ala Leu Tyr Arg Thr Asp Tyr Ser Gly Arg Gly Glu Leu Ser Ala
225                 230                 235                 240

Arg Gln Met His Leu Ala Arg Phe Leu Arg Met Leu Leu Arg Leu Ala
                245                 250                 255

Asp Glu Phe Gly Val Ala Val Val Ile Thr Asn Gln Val Val Ala Gln
            260                 265                 270

Val Asp Gly Ala Ala Met Phe Ala Ala Asp Pro Lys Lys Pro Ile Gly
        275                 280                 285

Gly Asn Ile Ile Ala His Ala Ser Thr Thr Arg Leu Tyr Leu Arg Lys
    290                 295                 300

Gly Arg Gly Glu Thr Arg Ile Cys Lys Ile Tyr Asp Ser Pro Cys Leu
305                 310                 315                 320

Pro Glu Ala Glu Ala Met Phe Ala Ile Asn Ala Asp Gly Val Gly Asp
                325                 330                 335

Ala Lys Asp
```

<210> SEQ ID NO 19
<211> LENGTH: 31
<212> TYPE: PRT
<213> ORGANISM: Homo sapiens

<400> SEQUENCE: 19

Lys Glu Pro Thr Leu Leu Gly Phe His Thr Ala Ser Gly Lys Lys Val
1               5                   10                  15

Lys Ile Ala Lys Glu Ser Leu Asp Lys Val Lys Asn Leu Phe Asp
            20                  25                  30

<210> SEQ ID NO 20
<211> LENGTH: 255
<212> TYPE: PRT
<213> ORGANISM: Artificial Sequence
<220> FEATURE:
<223> OTHER INFORMATION: Synthetic Construct

<400> SEQUENCE: 20

Gly Phe Thr Thr Ala Thr Glu Phe His Gln Arg Arg Ser Glu Ile Ile
1               5                   10                  15

Gln Ile Thr Thr Gly Ser Lys Glu Leu Asp Lys Leu Gln Gly Gly
            20                  25                  30

Ile Glu Thr Gly Ser Ile Thr Glu Met Phe Gly Glu Phe Arg Thr Gly
        35                  40                  45

Lys Thr Gln Ile Cys His Thr Leu Ala Val Thr Cys Gln Leu Pro Ile
    50                  55                  60

Asp Arg Gly Gly Gly Glu Gly Lys Ala Met Tyr Ile Asp Thr Glu Gly
65                  70                  75                  80

Thr Phe Arg Pro Glu Arg Leu Leu Ala Val Ala Glu Arg Tyr Gly Leu
                85                  90                  95

Ser Gly Ser Asp Val Leu Asp Asn Val Ala Tyr Ala Arg Ala Phe Asn
            100                 105                 110

Thr Asp His Gln Thr Gln Leu Leu Tyr Gln Ala Ser Ala Met Met Val
        115                 120                 125

Glu Ser Arg Tyr Ala Leu Leu Ile Val Asp Ser Ala Thr Ala Leu Tyr
    130                 135                 140

Arg Thr Asp Tyr Ser Gly Arg Gly Glu Leu Ser Ala Arg Gln Met His
145                 150                 155                 160

Leu Ala Arg Phe Leu Arg Met Leu Leu Arg Leu Ala Asp Glu Phe Gly
                165                 170                 175

Val Ala Val Val Ile Thr Asn Gln Val Val Ala Gln Val Asp Gly Ala
            180                 185                 190

Ala Met Phe Ala Ala Asp Pro Lys Lys Pro Ile Gly Gly Asn Ile Ile
        195                 200                 205

Ala His Ala Ser Thr Thr Arg Leu Tyr Leu Arg Lys Gly Arg Gly Glu
    210                 215                 220

Thr Arg Ile Cys Lys Ile Tyr Asp Ser Pro Cys Leu Pro Glu Ala Glu
225                 230                 235                 240

Ala Met Phe Ala Ile Asn Ala Asp Gly Val Gly Asp Ala Lys Asp
                245                 250                 255

<210> SEQ ID NO 21
<211> LENGTH: 340
<212> TYPE: PRT
<213> ORGANISM: Homo sapiens

<400> SEQUENCE: 21

Met Lys Glu Asp Gln Val Val Ala Glu Pro Gly Phe Gln Asp Glu
1               5                   10                  15

Glu Glu Ser Leu Phe Gln Asp Ile Asp Leu Leu Gln Lys His Gly Ile
            20                  25                  30

Asn Val Ala Asp Ile Lys Lys Leu Lys Ser Val Gly Ile Cys Thr Ile
            35                  40                  45

Lys Gly Ile Gln Met Thr Thr Arg Arg Ala Leu Cys Asn Val Lys Gly
50                  55                  60

Leu Ser Glu Ala Lys Val Asp Lys Ile Lys Glu Ala Ala Asn Lys Leu
65                  70                  75                  80

Ile Glu Pro Gly Phe Leu Thr Ala Phe Glu Tyr Ser Glu Lys Arg Lys
                85                  90                  95

Met Val Phe His Ile Thr Thr Gly Ser Gln Glu Phe Lys Leu Leu
            100                 105                 110

Gly Gly Gly Ile Glu Ser Met Ala Ile Thr Glu Ala Phe Gly Glu Phe
            115                 120                 125

Arg Thr Gly Lys Thr Gln Leu Ser His Thr Leu Cys Val Thr Ala Gln
130                 135                 140

Leu Pro Gly Ala Gly Gly Tyr Pro Gly Gly Lys Ile Ile Phe Ile Asp
145                 150                 155                 160

Thr Glu Asn Thr Phe Arg Pro Asp Arg Leu Arg Asp Ile Ala Asp Arg
                165                 170                 175

Phe Asn Val Asp His Asp Ala Val Leu Asp Asn Val Leu Tyr Ala Arg
            180                 185                 190

Ala Tyr Thr Ser Glu His Gln Met Glu Leu Leu Asp Tyr Val Ala Ala
            195                 200                 205

Lys Phe His Glu Glu Ala Gly Ile Phe Lys Leu Leu Ile Ile Asp Ser
210                 215                 220

Ile Met Ala Leu Phe Arg Val Asp Phe Ser Gly Arg Gly Glu Leu Ala
225                 230                 235                 240

Glu Arg Gln Gln Lys Leu Ala Gln Met Leu Ser Arg Leu Gln Lys Ile
                245                 250                 255

Ser Glu Glu Tyr Asn Val Ala Val Phe Val Thr Asn Gln Met Thr Ala
            260                 265                 270

Asp Pro Gly Ala Thr Met Thr Phe Gln Ala Asp Pro Lys Lys Pro Ile
            275                 280                 285

Gly Gly His Ile Leu Ala His Ala Ser Thr Thr Arg Ile Ser Leu Arg
290                 295                 300

Lys Gly Arg Gly Glu Leu Arg Ile Ala Lys Ile Tyr Asp Ser Pro Glu
305                 310                 315                 320

Met Pro Glu Asn Glu Ala Thr Phe Ala Ile Thr Ala Gly Gly Ile Gly
                325                 330                 335

Asp Ala Lys Glu
            340

<210> SEQ ID NO 22
<211> LENGTH: 432
<212> TYPE: PRT
<213> ORGANISM: Artificial Sequence
<220> FEATURE:
<223> OTHER INFORMATION: Synthetic Construct

<400> SEQUENCE: 22

Met Asp Thr Ile His His His His His His Asn Thr Ser Met Lys Ile

```
1               5                   10                  15
Glu Glu Gly Lys Leu Val Ile Trp Ile Asn Gly Asp Lys Gly Tyr Asn
                20                  25                  30
Gly Leu Ala Glu Val Gly Lys Lys Phe Glu Lys Asp Thr Gly Ile Lys
                35                  40                  45
Val Thr Val Glu His Pro Asp Lys Leu Glu Glu Lys Phe Pro Gln Val
50                  55                  60
Ala Ala Thr Gly Asp Gly Pro Asp Ile Ile Phe Trp Ala His Asp Arg
65                  70                  75                  80
Phe Gly Gly Tyr Ala Gln Ser Gly Leu Leu Ala Glu Ile Thr Pro Asp
                85                  90                  95
Lys Ala Phe Gln Asp Lys Leu Tyr Pro Phe Thr Trp Asp Ala Val Arg
                100                 105                 110
Tyr Asn Gly Lys Leu Ile Ala Tyr Pro Ile Ala Val Glu Ala Leu Ser
                115                 120                 125
Leu Ile Tyr Asn Lys Asp Leu Leu Pro Asn Pro Pro Lys Thr Trp Glu
130                 135                 140
Glu Ile Pro Ala Leu Asp Lys Glu Leu Lys Ala Lys Gly Lys Ser Ala
145                 150                 155                 160
Leu Met Phe Asn Leu Gln Glu Pro Tyr Phe Thr Trp Pro Leu Ile Ala
                165                 170                 175
Ala Asp Gly Gly Tyr Ala Phe Lys Tyr Glu Asn Gly Lys Tyr Asp Ile
                180                 185                 190
Lys Asp Val Gly Val Asp Asn Ala Gly Ala Lys Ala Gly Leu Thr Phe
                195                 200                 205
Leu Val Asp Leu Ile Lys Asn Lys His Met Asn Ala Asp Thr Asp Tyr
210                 215                 220
Ser Ile Ala Glu Ala Ala Phe Asn Lys Gly Glu Thr Ala Met Thr Ile
225                 230                 235                 240
Asn Gly Pro Trp Ala Trp Ser Asn Ile Asp Thr Ser Lys Val Asn Tyr
                245                 250                 255
Gly Val Thr Val Leu Pro Thr Phe Lys Gly Gln Pro Ser Lys Pro Phe
                260                 265                 270
Val Gly Val Leu Ser Ala Gly Ile Asp Ala Ala Ser Pro Asn Lys Glu
                275                 280                 285
Leu Ala Lys Glu Phe Leu Glu Asn Tyr Leu Leu Thr Asp Glu Gly Leu
                290                 295                 300
Glu Ala Val Asn Lys Asp Lys Pro Leu Gly Ala Val Ala Leu Lys Ser
305                 310                 315                 320
Tyr Glu Glu Glu Leu Ala Lys Asp Pro Arg Ile Ala Ala Thr Met Glu
                325                 330                 335
Asn Ala Gln Lys Gly Glu Ile Met Pro Asn Ile Pro Gln Met Ser Ala
                340                 345                 350
Phe Trp Tyr Ala Val Arg Thr Ala Val Ile Asn Ala Ala Ser Gly Arg
                355                 360                 365
Gln Thr Val Asp Glu Ala Leu Lys Asp Ala Gln Thr Asn Ser Ser Ser
                370                 375                 380
Thr Ser Gly Ser Gly Gly Ala Arg Leu Glu Asn Leu Tyr Phe Gln Gly
385                 390                 395                 400
Ser Lys Glu Pro Thr Leu Leu Gly Phe His Thr Ala Ser Gly Lys Lys
                405                 410                 415
Val Lys Ile Ala Lys Glu Ser Leu Asp Lys Val Lys Asn Leu Phe Asp
                420                 425                 430
```

<210> SEQ ID NO 23
<211> LENGTH: 696
<212> TYPE: PRT
<213> ORGANISM: Artificial Sequence
<220> FEATURE:
<223> OTHER INFORMATION: Synthetic Construct

<400> SEQUENCE: 23

```
Met Asp Thr Ile His His His His His Asn Thr Ser Met Lys Ile
1               5                   10                  15

Glu Glu Gly Lys Leu Val Ile Trp Ile Asn Gly Asp Lys Gly Tyr Asn
            20                  25                  30

Gly Leu Ala Glu Val Gly Lys Lys Phe Glu Lys Asp Thr Gly Ile Lys
        35                  40                  45

Val Thr Val Glu His Pro Asp Lys Leu Glu Glu Lys Phe Pro Gln Val
    50                  55                  60

Ala Ala Thr Gly Asp Gly Pro Asp Ile Ile Phe Trp Ala His Asp Arg
65                  70                  75                  80

Phe Gly Gly Tyr Ala Gln Ser Gly Leu Leu Ala Glu Ile Thr Pro Asp
                85                  90                  95

Lys Ala Phe Gln Asp Lys Leu Tyr Pro Phe Thr Trp Asp Ala Val Arg
            100                 105                 110

Tyr Asn Gly Lys Leu Ile Ala Tyr Pro Ile Ala Val Glu Ala Leu Ser
        115                 120                 125

Leu Ile Tyr Asn Lys Asp Leu Leu Pro Asn Pro Pro Lys Thr Trp Glu
    130                 135                 140

Glu Ile Pro Ala Leu Asp Lys Glu Leu Lys Ala Lys Gly Lys Ser Ala
145                 150                 155                 160

Leu Met Phe Asn Leu Gln Glu Pro Tyr Phe Thr Trp Pro Leu Ile Ala
                165                 170                 175

Ala Asp Gly Gly Tyr Ala Phe Lys Tyr Glu Asn Gly Lys Tyr Asp Ile
            180                 185                 190

Lys Asp Val Gly Val Asp Asn Ala Gly Ala Lys Ala Gly Leu Thr Phe
        195                 200                 205

Leu Val Asp Leu Ile Lys Asn Lys His Met Asn Ala Asp Thr Asp Tyr
    210                 215                 220

Ser Ile Ala Glu Ala Ala Phe Asn Lys Gly Glu Thr Ala Met Thr Ile
225                 230                 235                 240

Asn Gly Pro Trp Ala Trp Ser Asn Ile Asp Thr Ser Lys Val Asn Tyr
                245                 250                 255

Gly Val Thr Val Leu Pro Thr Phe Lys Gly Gln Pro Ser Lys Pro Phe
            260                 265                 270

Val Gly Val Leu Ser Ala Gly Ile Asp Ala Ala Ser Pro Asn Lys Glu
        275                 280                 285

Leu Ala Lys Glu Phe Leu Glu Asn Tyr Leu Leu Thr Asp Glu Gly Leu
    290                 295                 300

Glu Ala Val Asn Lys Asp Lys Pro Leu Gly Ala Val Ala Leu Lys Ser
305                 310                 315                 320

Tyr Glu Glu Glu Leu Ala Lys Asp Pro Arg Ile Ala Ala Thr Met Glu
                325                 330                 335

Asn Ala Gln Lys Gly Glu Ile Met Pro Asn Ile Pro Gln Met Ser Ala
            340                 345                 350

Phe Trp Tyr Ala Val Arg Thr Ala Val Ile Asn Ala Ala Ser Gly Arg
        355                 360                 365
```

Gln Thr Val Asp Glu Ala Leu Lys Asp Ala Gln Thr Asn Ser Ser Ser
    370                 375                 380

Thr Ser Gly Ser Gly Gly Ala Arg Leu Glu Asn Leu Tyr Phe Gln Gly
385                 390                 395                 400

Ser Lys Glu Pro Thr Leu Leu Gly Phe His Thr Ala Ser Gly Lys Lys
            405                 410                 415

Val Lys Ile Ala Lys Glu Ser Leu Asp Lys Val Lys Asn Leu Phe Asp
        420                 425                 430

Thr Gly Ser Thr Gly Ser Thr Gly Ser Gly Phe Thr Thr Ala Thr Glu
    435                 440                 445

Phe His Gln Arg Arg Ser Glu Ile Ile Gln Ile Thr Thr Gly Ser Lys
450                 455                 460

Glu Leu Asp Lys Leu Leu Gln Gly Gly Ile Glu Thr Gly Ser Ile Thr
465                 470                 475                 480

Glu Met Phe Gly Glu Phe Arg Thr Gly Lys Thr Gln Ile Cys His Thr
            485                 490                 495

Leu Ala Val Thr Cys Gln Leu Pro Ile Asp Arg Gly Gly Gly Glu Gly
        500                 505                 510

Lys Ala Met Tyr Ile Asp Thr Glu Gly Thr Phe Arg Pro Glu Arg Leu
    515                 520                 525

Leu Ala Val Ala Glu Arg Tyr Gly Leu Ser Gly Ser Asp Val Leu Asp
530                 535                 540

Asn Val Ala Tyr Ala Arg Ala Phe Asn Thr Asp His Gln Thr Gln Leu
545                 550                 555                 560

Leu Tyr Gln Ala Ser Ala Met Met Val Glu Ser Arg Tyr Ala Leu Leu
            565                 570                 575

Ile Val Asp Ser Ala Thr Ala Leu Tyr Arg Thr Asp Tyr Ser Gly Arg
        580                 585                 590

Gly Glu Leu Ser Ala Arg Gln Met His Leu Ala Arg Phe Leu Arg Met
    595                 600                 605

Leu Leu Arg Leu Ala Asp Glu Phe Gly Val Ala Val Val Ile Thr Asn
610                 615                 620

Gln Val Val Ala Gln Val Asp Gly Ala Ala Met Phe Ala Ala Asp Pro
625                 630                 635                 640

Lys Lys Pro Ile Gly Gly Asn Ile Ile Ala His Ala Ser Thr Thr Arg
            645                 650                 655

Leu Tyr Leu Arg Lys Gly Arg Gly Glu Thr Arg Ile Cys Lys Ile Tyr
        660                 665                 670

Asp Ser Pro Cys Leu Pro Glu Ala Glu Ala Met Phe Ala Ile Asn Ala
    675                 680                 685

Asp Gly Val Gly Asp Ala Lys Asp
    690                 695

<210> SEQ ID NO 24
<211> LENGTH: 597
<212> TYPE: DNA
<213> ORGANISM: Artificial Sequence
<220> FEATURE:
<223> OTHER INFORMATION: Synthetic Construct

<400> SEQUENCE: 24
gccataccgc gaaaggtttt gcgccattcg atggtgtccg ggatctcgac gctctccctt     60
atgcgactcc tgcattagga aattaatacg actcactata ggggaattgt gagcggataa    120
caattcccct gtagaaataa ttttgtttaa ctttaataag gagatatacc atgggcagca    180

```
gccatcacca tcatcaccac agccaggatc cgaattcgag ctcggcgcgc ctgcaggtcg    240
acaagcttgc ggccgcataa tgcttaagtc gaacagaaag taatcgtatt gtacacggcc    300
gcataatcga aattaatacg actcactata ggggaattgt gagcggataa caattcccca    360
tcttagtata ttagttaagt ataagaagga gatatacata tggcagatct caattggata    420
tcggccggcc acgcgatcgc tgacgtcggt accctcgagt ctggtaaaga aaccgctgct    480
gcgaaatttg aacgccagca catggactcg tctactagcg cagcttaatt aacctaggct    540
gctgccaccg ctgagcaata actagcataa ccccttgggg cctctaaacg ggtcttg      597
```

<210> SEQ ID NO 25
<211> LENGTH: 432
<212> TYPE: PRT
<213> ORGANISM: Artificial Sequence
<220> FEATURE:
<223> OTHER INFORMATION: Synthetic Construct

<400> SEQUENCE: 25

```
Met Asp Thr Ile His His His His His His Asn Thr Ser Met Lys Ile
1               5                   10                  15

Glu Glu Gly Lys Leu Val Ile Trp Ile Asn Gly Asp Lys Gly Tyr Asn
            20                  25                  30

Gly Leu Ala Glu Val Gly Lys Lys Phe Glu Lys Asp Thr Gly Ile Lys
        35                  40                  45

Val Thr Val Glu His Pro Asp Lys Leu Glu Glu Lys Phe Pro Gln Val
    50                  55                  60

Ala Ala Thr Gly Asp Gly Pro Asp Ile Ile Phe Trp Ala His Asp Arg
65                  70                  75                  80

Phe Gly Gly Tyr Ala Gln Ser Gly Leu Leu Ala Glu Ile Thr Pro Asp
                85                  90                  95

Lys Ala Phe Gln Asp Lys Leu Tyr Pro Phe Thr Trp Asp Ala Val Arg
            100                 105                 110

Tyr Asn Gly Lys Leu Ile Ala Tyr Pro Ile Ala Val Glu Ala Leu Ser
        115                 120                 125

Leu Ile Tyr Asn Lys Asp Leu Leu Pro Asn Pro Lys Thr Trp Glu
    130                 135                 140

Glu Ile Pro Ala Leu Asp Lys Glu Leu Lys Ala Lys Gly Lys Ser Ala
145                 150                 155                 160

Leu Met Phe Asn Leu Gln Glu Pro Tyr Phe Thr Trp Pro Leu Ile Ala
                165                 170                 175

Ala Asp Gly Gly Tyr Ala Phe Lys Tyr Glu Asn Gly Lys Tyr Asp Ile
            180                 185                 190

Lys Asp Val Gly Val Asp Asn Ala Gly Ala Lys Ala Gly Leu Thr Phe
        195                 200                 205

Leu Val Asp Leu Ile Lys Asn Lys His Met Asn Ala Asp Thr Asp Tyr
    210                 215                 220

Ser Ile Ala Glu Ala Ala Phe Asn Lys Gly Glu Thr Ala Met Thr Ile
225                 230                 235                 240

Asn Gly Pro Trp Ala Trp Ser Asn Ile Asp Thr Ser Lys Val Asn Tyr
                245                 250                 255

Gly Val Thr Val Leu Pro Thr Phe Lys Gly Gln Pro Ser Lys Pro Phe
            260                 265                 270

Val Gly Val Leu Ser Ala Gly Ile Asp Ala Ala Ser Pro Asn Lys Glu
        275                 280                 285
```

```
Leu Ala Lys Glu Phe Leu Glu Asn Tyr Leu Leu Thr Asp Glu Gly Leu
    290                 295                 300

Glu Ala Val Asn Lys Asp Lys Pro Leu Gly Ala Val Ala Leu Lys Ser
305                 310                 315                 320

Tyr Glu Glu Leu Ala Lys Asp Pro Arg Ile Ala Ala Thr Met Glu
                325                 330                 335

Asn Ala Gln Lys Gly Glu Ile Met Pro Asn Ile Pro Gln Met Ser Ala
                340                 345                 350

Phe Trp Tyr Ala Val Arg Thr Ala Val Ile Asn Ala Ala Ser Gly Arg
                355                 360                 365

Gln Thr Val Asp Glu Ala Leu Lys Asp Ala Gln Thr Asn Ser Ser Ser
    370                 375                 380

Thr Ser Gly Ser Gly Gly Ala Arg Leu Glu Asn Leu Tyr Phe Gln Gly
385                 390                 395                 400

Ser Lys Glu Pro Thr Leu Leu Gly Trp His Thr Ala Ser Gly Lys Lys
                405                 410                 415

Val Lys Ile Ala Lys Glu Ser Leu Asp Lys Val Lys Asn Leu Phe Asp
                420                 425                 430
```

<210> SEQ ID NO 26
<211> LENGTH: 432
<212> TYPE: PRT
<213> ORGANISM: Artificial Sequence
<220> FEATURE:
<223> OTHER INFORMATION: Synthetic Construct

<400> SEQUENCE: 26

```
Met Asp Thr Ile His His His His His His Asn Thr Ser Met Lys Ile
1               5                   10                  15

Glu Glu Gly Lys Leu Val Ile Trp Ile Asn Gly Asp Lys Gly Tyr Asn
                20                  25                  30

Gly Leu Ala Glu Val Gly Lys Lys Phe Glu Lys Asp Thr Gly Ile Lys
            35                  40                  45

Val Thr Val Glu His Pro Asp Lys Leu Glu Glu Lys Phe Pro Gln Val
    50                  55                  60

Ala Ala Thr Gly Asp Gly Pro Asp Ile Ile Phe Trp Ala His Asp Arg
65                  70                  75                  80

Phe Gly Gly Tyr Ala Gln Ser Gly Leu Leu Ala Glu Ile Thr Pro Asp
                85                  90                  95

Lys Ala Phe Gln Asp Lys Leu Tyr Pro Phe Thr Trp Asp Ala Val Arg
                100                 105                 110

Tyr Asn Gly Lys Leu Ile Ala Tyr Pro Ile Ala Val Glu Ala Leu Ser
                115                 120                 125

Leu Ile Tyr Asn Lys Asp Leu Leu Pro Asn Pro Pro Lys Thr Trp Glu
    130                 135                 140

Glu Ile Pro Ala Leu Asp Lys Glu Leu Lys Ala Lys Gly Lys Ser Ala
145                 150                 155                 160

Leu Met Phe Asn Leu Gln Glu Pro Tyr Phe Thr Trp Pro Leu Ile Ala
                165                 170                 175

Ala Asp Gly Gly Tyr Ala Phe Lys Tyr Glu Asn Gly Lys Tyr Asp Ile
                180                 185                 190

Lys Asp Val Gly Val Asp Asn Ala Gly Ala Lys Ala Gly Leu Thr Phe
            195                 200                 205

Leu Val Asp Leu Ile Lys Asn Lys His Met Asn Ala Asp Thr Asp Tyr
    210                 215                 220
```

```
Ser Ile Ala Glu Ala Ala Phe Asn Lys Gly Glu Thr Ala Met Thr Ile
225                 230                 235                 240

Asn Gly Pro Trp Ala Trp Ser Asn Ile Asp Thr Ser Lys Val Asn Tyr
            245                 250                 255

Gly Val Thr Val Leu Pro Thr Phe Lys Gly Gln Pro Ser Lys Pro Phe
        260                 265                 270

Val Gly Val Leu Ser Ala Gly Ile Asp Ala Ala Ser Pro Asn Lys Glu
    275                 280                 285

Leu Ala Lys Glu Phe Leu Glu Asn Tyr Leu Leu Thr Asp Glu Gly Leu
290                 295                 300

Glu Ala Val Asn Lys Asp Lys Pro Leu Gly Ala Val Ala Leu Lys Ser
305                 310                 315                 320

Tyr Glu Glu Leu Ala Lys Asp Pro Arg Ile Ala Ala Thr Met Glu
            325                 330                 335

Asn Ala Gln Lys Gly Glu Ile Met Pro Asn Ile Pro Gln Met Ser Ala
            340                 345                 350

Phe Trp Tyr Ala Val Arg Thr Ala Val Ile Asn Ala Ala Ser Gly Arg
        355                 360                 365

Gln Thr Val Asp Glu Ala Leu Lys Asp Ala Gln Thr Asn Ser Ser Ser
370                 375                 380

Thr Ser Gly Ser Gly Gly Ala Arg Leu Glu Asn Leu Tyr Phe Gln Gly
385                 390                 395                 400

Ser Lys Glu Pro Thr Leu Leu Gly Phe His Thr Ser Ser Gly Lys Lys
            405                 410                 415

Val Lys Ile Ala Lys Glu Ser Leu Asp Lys Val Lys Asn Leu Phe Asp
        420                 425                 430

<210> SEQ ID NO 27
<211> LENGTH: 322
<212> TYPE: PRT
<213> ORGANISM: Methanococcus voltae
<220> FEATURE:
<221> NAME/KEY: RadA
<222> LOCATION: (107)..(110)

<400> SEQUENCE: 27

Met Ser Asp Asn Leu Thr Asp Leu Pro Gly Val Gly Pro Ser Thr Ala
1               5                   10                  15

Glu Lys Leu Val Glu Ala Gly Tyr Ile Asp Phe Met Lys Ile Ala Thr
            20                  25                  30

Ala Thr Val Gly Glu Leu Thr Asp Ile Glu Gly Ile Ser Glu Lys Ala
        35                  40                  45

Ala Ala Lys Met Ile Met Gly Ala Arg Asp Leu Cys Asp Leu Gly Phe
50                  55                  60

Lys Ser Gly Ile Asp Leu Leu Lys Gln Arg Ser Thr Val Trp Lys Leu
65                  70                  75                  80

Ser Thr Ser Ser Ser Glu Leu Asp Ser Val Leu Gly Gly Gly Leu Glu
                85                  90                  95

Ser Gln Ser Val Thr Glu Phe Ala Gly Val Phe Gly Ser Gly Lys Thr
            100                 105                 110

Gln Ile Met His Gln Ser Cys Val Asn Leu Gln Asn Pro Glu Phe Leu
        115                 120                 125

Phe Tyr Asp Glu Glu Ala Val Ser Lys Gly Glu Val Ala Gln Pro Lys
130                 135                 140

Ala Val Tyr Ile Asp Thr Glu Gly Thr Phe Arg Pro Glu Arg Ile Met
145                 150                 155                 160
```

```
Gln Met Ala Glu His Ala Gly Ile Asp Gly Gln Thr Val Leu Asp Asn
                165                 170                 175

Thr Phe Val Ala Arg Ala Tyr Asn Ser Asp Met Gln Met Leu Phe Ala
            180                 185                 190

Glu Lys Ile Glu Asp Leu Ile Gln Glu Gly Asn Asn Ile Lys Leu Val
        195                 200                 205

Val Ile Asp Ser Leu Thr Ser Thr Phe Arg Asn Glu Tyr Thr Gly Arg
210                 215                 220

Gly Lys Leu Ala Glu Arg Gln Gln Lys Leu Gly Arg His Met Ala Thr
225                 230                 235                 240

Leu Asn Lys Leu Ala Asp Leu Phe Asn Cys Val Val Leu Val Thr Asn
                245                 250                 255

Gln Val Ser Ala Lys Pro Asp Ala Phe Phe Gly Met Ala Glu Gln Ala
            260                 265                 270

Ile Gly Gly His Ile Val Gly His Ala Ala Thr Phe Arg Phe Phe Val
        275                 280                 285

Arg Lys Gly Lys Gly Asp Lys Arg Val Ala Lys Leu Tyr Asp Ser Pro
290                 295                 300

His Leu Pro Asp Ala Glu Ala Ile Phe Arg Ile Thr Glu Lys Gly Ile
305                 310                 315                 320

Gln Asp

<210> SEQ ID NO 28
<211> LENGTH: 1155
<212> TYPE: PRT
<213> ORGANISM: Arabidopsis thaliana
<220> FEATURE:
<221> NAME/KEY: BRC_At
<222> LOCATION: (70)..(73)

<400> SEQUENCE: 28

Met Ser Thr Trp His Leu Phe Ser Asp Ser Gly Asp Gly Phe Arg
1               5                   10                  15

Trp Glu Val Ala Gly Arg Ile Leu Gln Ser Val Ser Asp Ser Thr Pro
            20                  25                  30

Thr Lys Ala Leu Glu Ser Thr Ala Pro Leu Pro Ser Met Ala Asp Leu
        35                  40                  45

Leu Leu Gln Gly Cys Ser Lys Leu Ile Glu Arg Glu Ser Met Pro
    50                  55                  60

Gly Glu Ile Pro Met Phe Arg Thr Gly Leu Gly Lys Ser Val Val Leu
65                  70                  75                  80

Lys Glu Ser Ser Ile Ala Lys Ala Lys Ser Ile Leu Ala Glu Asn Val
                85                  90                  95

Ala Tyr Ser Asp Leu Gln Asn Thr Asn Cys Ser Ile Pro Gln Thr Arg
            100                 105                 110

Gln Val Asp Thr Ala Glu Thr Met Pro Met Phe Arg Thr Ala Leu Gly
        115                 120                 125

Lys Thr Val Pro Leu Lys Glu Ser Ile Ala Lys Pro Leu Ser Ile
130                 135                 140

Leu Gly Ser Asp Met Ile Ile Asp Ser Asp Asn Val Leu Pro Arg Glu
145                 150                 155                 160

Ser Gly Phe Gly Val Pro Asn Ser Leu Phe Gln Thr Ala Ser Asn Lys
                165                 170                 175

Lys Val Asn Val Ser Ser Ala Gly Leu Ala Arg Ala Lys Ala Leu Leu
            180                 185                 190
```

```
Gly Leu Glu Glu Asp Asp Leu Asn Gly Phe Asn His Val Asn Gln Ser
            195                 200                 205

Ser Ser Ser Leu Gln Gln His Gly Trp Ser Gly Leu Lys Thr His Glu
    210                 215                 220

Glu Phe Asp Ala Thr Val Val Lys His His Ser Gly Thr Pro Gly Gln
225                 230                 235                 240

Tyr Glu Asn Tyr Val Ser Gly Lys Arg Ser Glu Ile Leu Asn Pro Ser
                245                 250                 255

Leu Lys Val Pro Pro Thr Lys Phe Gln Thr Ala Gly Gly Lys Ser Leu
                260                 265                 270

Ser Val Ser Ala Glu Ala Leu Lys Arg Ala Arg Asn Leu Leu Gly Asp
            275                 280                 285

Pro Glu Leu Gly Ser Phe Phe Asp Asp Val Ala Gly Gly Asp Gln Phe
        290                 295                 300

Phe Thr Pro Gln Lys Asp Glu Arg Leu Ser Asp Ile Ala Ile Asn Asn
305                 310                 315                 320

Gly Ser Val Asn Thr Gly Tyr Ile Ala His Glu Lys Thr Ser Asn
                325                 330                 335

Lys His Thr Ser Asn Ser Phe Val Ser Pro Leu His Ser Ser Lys
            340                 345                 350

Gln Phe Arg Ser Val Asn Leu Glu Asn Leu Ala Ser Gly Gly Asn Leu
        355                 360                 365

Ile Lys Lys Phe Asp Thr Ala Val Asp Glu Thr Asn Cys Ala Leu Asn
370                 375                 380

Ile Ser Lys Pro Ala Thr His Gly Leu Ser Asn Asn Arg Pro Leu Ala
385                 390                 395                 400

Ser Asp Met Ala Val Asn Asn Ser Lys Gly Asn Gly Phe Ile Pro Arg
                405                 410                 415

Ala Arg Gln Leu Gly Arg Pro Ala Asp Gln Pro Leu Val Asp Ile Thr
            420                 425                 430

Asn Arg Arg Asp Thr Ala Tyr Ala Asn Asn Lys Gln Asp Ser Thr Gln
        435                 440                 445

Lys Lys Arg Leu Gly Lys Thr Val Ser Val Ser Pro Phe Lys Arg Pro
450                 455                 460

Arg Ile Ser Ser Phe Lys Thr Pro Leu Lys Lys Asn Ala Gln Gln Ala
465                 470                 475                 480

Ser Ser Gly Leu Ser Val Val Ser Cys Asp Thr Leu Thr Ser Lys Lys
                485                 490                 495

Val Leu Ser Thr Arg Tyr Pro Glu Lys Ser Pro Arg Val Tyr Ile Lys
            500                 505                 510

Glu Phe Phe Gly Met His Pro Thr Ala Thr Thr Arg Met Asp Tyr Val
        515                 520                 525

Pro Asp His Val Arg Arg Ile Lys Ser Ser Asn Ala Asp Lys Tyr Val
530                 535                 540

Phe Cys Asp Glu Ser Ser Ser Asn Lys Val Gly Ala Glu Thr Phe Leu
545                 550                 555                 560

Gln Met Leu Ala Glu Ser Gly Ala Ser Leu Gln His Ala Ser Arg Lys
                565                 570                 575

Trp Val Thr Asn His Tyr Arg Trp Ile Val Trp Lys Leu Ala Cys Tyr
            580                 585                 590

Asp Ile Tyr Tyr Pro Ala Lys Cys Arg Gly Asn Phe Leu Thr Ile Thr
        595                 600                 605
```

```
Asn Val Leu Glu Glu Leu Lys Tyr Arg Tyr Glu Arg Glu Val Asn His
    610                 615                 620

Gly His Cys Ser Ala Ile Lys Arg Ile Leu Ser Gly Asp Ala Pro Ala
625                 630                 635                 640

Ser Ser Met Met Val Leu Cys Ile Ser Ala Ile Asn Pro Arg Thr Asp
                645                 650                 655

Asn Gly Ser Gln Glu Ala His Cys Ser Asp Asn Cys Ser Asn Val Lys
            660                 665                 670

Val Glu Leu Thr Asp Gly Trp Tyr Ser Met Asn Ala Ala Leu Asp Val
        675                 680                 685

Val Leu Thr Lys Gln Leu Asn Ala Gly Lys Leu Phe Val Gly Gln Lys
    690                 695                 700

Leu Arg Ile Leu Gly Ala Gly Leu Ser Gly Trp Ala Thr Pro Thr Ser
705                 710                 715                 720

Pro Leu Glu Ala Val Ile Ser Ser Thr Ile Cys Leu Leu Leu Asn Ile
                725                 730                 735

Asn Gly Thr Tyr Arg Ala His Trp Ala Asp Arg Leu Gly Phe Cys Lys
            740                 745                 750

Glu Ile Gly Val Pro Leu Ala Phe Asn Cys Ile Lys Cys Asn Gly Gly
        755                 760                 765

Pro Val Pro Lys Thr Leu Ala Gly Ile Thr Arg Ile Tyr Pro Ile Leu
    770                 775                 780

Tyr Lys Glu Arg Leu Gly Glu Lys Lys Ser Ile Val Arg Ser Glu Arg
785                 790                 795                 800

Ile Glu Ser Arg Ile Ile Gln Leu His Asn Gln Arg Arg Ser Ala Leu
                805                 810                 815

Val Glu Gly Ile Met Cys Glu Tyr Gln Arg Gly Ile Asn Gly Val His
            820                 825                 830

Ser Gln Asn Asp Thr Asp Ser Glu Glu Gly Ala Lys Val Phe Lys Leu
        835                 840                 845

Leu Glu Thr Ala Ala Glu Pro Glu Leu Leu Met Ala Glu Met Ser Leu
    850                 855                 860

Glu Gln Leu Thr Ser Phe Thr Thr Tyr Lys Ala Lys Phe Glu Ala Ala
865                 870                 875                 880

Lys Gln Met Gln Met Glu Lys Ser Val Ala Lys Ala Leu Glu Asp Ala
                885                 890                 895

Gly Leu Gly Glu Arg Asn Val Thr Pro Phe Met Arg Ile Arg Leu Val
            900                 905                 910

Gly Leu Thr Ser Leu Ser Asn Glu Gly Glu His Asn Pro Lys Glu Gly
        915                 920                 925

Ile Val Thr Ile Trp Asp Pro Thr Glu Arg Gln Arg Thr Glu Leu Thr
    930                 935                 940

Glu Gly Lys Ile Tyr Ile Met Lys Gly Leu Val Pro Met Asn Ser Asp
945                 950                 955                 960

Ser Glu Thr Leu Tyr Leu His Ala Arg Gly Ser Ser Arg Trp Gln
                965                 970                 975

Pro Leu Ser Pro Lys Asp Ser Glu Asn Phe Gln Pro Phe Asn Pro
            980                 985                 990

Arg Lys Pro Ile Ser Leu Ser Asn Leu Gly Glu Ile Pro Leu Ser Ser
            995                 1000                1005

Glu Phe Asp Ile Ala Ala Tyr Val Val Tyr Val Gly Asp Ala Tyr
        1010                1015                1020

Thr Asp Val Leu Gln Lys Lys Gln Trp Val Phe Val Thr Asp Gly
```

-continued

```
            1025                1030                1035

Ser Thr Gln His Ser Gly Glu Ile Ser Asn Ser Leu Leu Ala Ile
        1040                1045                1050

Ser Phe Ser Thr Pro Phe Met Asp Asp Ser Ser Val Ser His Ile
    1055                1060                1065

Ser His Asn Leu Val Gly Ser Val Val Gly Phe Cys Asn Leu Ile
    1070                1075                1080

Lys Arg Ala Lys Asp Ala Thr Asn Glu Met Trp Val Ala Glu Thr
    1085                1090                1095

Thr Glu Asn Ser Val Tyr Phe Ile Asn Ala Glu Ala Ala Tyr Ser
    1100                1105                1110

Ser His Leu Lys Thr Arg Ser Ala His Ile Gln Thr Trp Ala Lys
    1115                1120                1125

Leu Tyr Ser Ser Lys Ser Val Ile His Glu Leu Arg Gln Arg Val
    1130                1135                1140

Leu Phe Ile Ile Gly Ala Cys Lys Ser Pro Ser Cys
    1145                1150                1155

<210> SEQ ID NO 29
<211> LENGTH: 1075
<212> TYPE: PRT
<213> ORGANISM: Ustilago maydis
<220> FEATURE:
<221> NAME/KEY: BRC_Um
<222> LOCATION: (294)..(297)
<300> PUBLICATION INFORMATION:
<313> RELEVANT RESIDUES IN SEQ ID NO: (294)..(297)

<400> SEQUENCE: 29

Met Ser Thr Ala Ser Pro Ser Val Ala His Ala Phe Pro Phe Gly Ser
1               5                   10                  15

Ala Asp Pro Leu Phe Asp Asp Ile Ala Ala Thr Gln Gln Ser Ile
            20                  25                  30

Leu Glu Glu Leu His Thr Ile Ser Glu Glu Ala Leu Ser Ala Asn Ser
            35                  40                  45

Asp His Ser Glu Ser His Ile Asn Ser His Ile Asp Gln Ser Tyr
        50                  55                  60

Gly Ala Glu Thr Gln Gly Glu His Asp Gly Ile His Ser Asp Ala Ser
65                  70                  75                  80

Ser Ser Gly Leu Ser Gln Leu Leu Met Ser Arg Phe Ala Ser Gln Gln
                85                  90                  95

Gly Ala Gln Leu Ser Ile Pro Ala Ser Ser Glu His Asn Met Glu His
            100                 105                 110

Ser Pro Ala Ala Pro His Ile Ala Glu Arg Ser Gly Phe Glu Gln Glu
        115                 120                 125

Ala Pro Ser Pro Thr Pro Pro Ile Met Ala Asp Gly Ser Glu Ile Thr
    130                 135                 140

Ser Gln Thr Ala Asp Asp Gly Thr Asn Ser Asn Val Val Lys Ile Thr
145                 150                 155                 160

Pro Leu Gln Ala Asp Ile Glu Glu Ser Val Val Thr Leu Glu Ser Leu
                165                 170                 175

Pro Gln Arg Ser Asp Pro Gln Ser Ala Thr Pro Leu Ser Ser Ser Ile
            180                 185                 190

Leu Ala Pro Thr Gln Thr Leu Asn Thr Thr Pro Glu Pro Pro Asp Ala
        195                 200                 205

Ala Pro Ser Gln Met Asp Ala Ser Phe Glu Leu Asp His Ala Asp Leu
```

```
              210                 215                 220
Phe Asp Gly Ile Glu Pro Asp Ala Phe Asp Asp Ile Glu Leu Ser Pro
225                 230                 235                 240

Pro Thr Arg Arg His Val Ala Leu Pro Leu Lys Glu Pro Pro Gln Ser
                245                 250                 255

Leu Ala Gly Leu Asp Ser Gly Leu Asp Ser Asp Glu Phe Ile Asn Asp
                260                 265                 270

Glu Ser Pro Gln Leu Pro Pro Gly Ser Gln Thr Met Ser Phe Leu Gln
                275                 280                 285

Pro Cys Phe Val Gly Phe Gln Thr Gly His Gly Lys Gln Val Lys Leu
        290                 295                 300

Ser Asp Lys Ala Leu Glu Lys Ala Arg Lys Leu Met Met Gln Leu Asp
305                 310                 315                 320

Asp Thr Thr Asp Leu Leu Pro Ala Gln Thr Ser Gln Ser Ser Leu
                325                 330                 335

His Lys Arg Ile His Thr Thr Gly Ser Leu Pro Gln Ala Leu Gln Ser
                340                 345                 350

Phe Gly Asn Ala Pro Ser Met Leu Ser Thr Val Thr Arg Thr Pro Met
        355                 360                 365

Gln Glu Ile Val Pro Lys Gln Arg Thr Ala Ala Ile Asn Glu Ser Glu
        370                 375                 380

Lys Cys Ala Leu Ala Glu Glu Asp Lys Val Ala Ser Val Gln Ala Thr
385                 390                 395                 400

Ser Gln Val Thr Ala Leu Pro Ala Ala Gln Ala Pro Thr Thr Arg Arg
                405                 410                 415

Ile Glu Pro His Pro Phe Thr Thr Pro Lys Gln Thr Arg Asn Gly Arg
                420                 425                 430

Leu Pro Val Arg Gln Asn Leu Ala Ser Pro Met Arg Thr Pro Ala Thr
                435                 440                 445

Ala Pro Gly Leu Arg Phe Thr Thr Pro Gln Pro Ser Lys Arg Ile Ser
        450                 455                 460

Leu Gly Met Leu Pro Arg Ala Glu Ile Gly Gly Ser Ser Thr Gly
465                 470                 475                 480

Ser Lys Arg Thr Leu Pro Arg Phe Val Thr Pro Phe Lys Gly Gly Lys
                485                 490                 495

Arg Pro Arg Thr Glu Asp Leu Gln Asp Leu Ala Ser Pro Leu Arg Arg
                500                 505                 510

Leu Asp Arg Ala Gln Ala Gln Ser Leu Ser Arg Ala Ser Pro Ile Ser
                515                 520                 525

Pro Arg Gln Ser Phe Ser Met Arg Gln Ala Ser Ser Asn Ile Ser Lys
        530                 535                 540

Gly Ser Ala Val Phe Cys Met Gln His Asp Gly Pro Arg His Lys Leu
545                 550                 555                 560

Ala Ala Val Gly Arg Pro Glu Tyr Tyr Ser Ser Met Gln Met Ile Ala
                565                 570                 575

Lys Gly Val Pro Asp Glu Val Leu Val Leu Lys Asp Ala Ser Gln
                580                 585                 590

Ala Ala Arg Tyr Ala Phe Glu Gly Pro Asp Ser Ala Leu Leu Met Gln
        595                 600                 605

Gln Gln Ala Leu Glu Glu Leu His Ala Arg Gly Cys Ser Asn Ala Asp
        610                 615                 620

Met Pro Trp Val Gln Asn His Trp Thr Leu Ile Leu Trp Lys Leu Ala
625                 630                 635                 640
```

```
Ala Met Val Arg Leu Glu Pro Ser Ser Ala Ser Asn Arg Trp Ser Trp
            645                 650                 655

Asn Glu Leu Ile Arg Gln Leu Leu Tyr Arg Tyr Glu Arg Glu Val Asn
            660                 665                 670

Leu Ala Gln Arg Ser Cys Leu Lys Arg Ile Gln Glu His Asp Ser Ser
            675                 680                 685

Ala Ala Arg Pro Met Val Leu Met Val Ser Lys Ile Leu Glu Glu Glu
            690                 695                 700

Ile Glu Val Gln Ser Pro Ser Gly Glu Ile Val Ser Arg Ile Cys Thr
705                 710                 715                 720

Ile Leu Glu Leu Ser Asp Gly Trp Tyr Arg Ile Leu Ala Gln Ile Asp
            725                 730                 735

Ser Val Leu Thr Asn Ala Cys Gln Arg Gly Arg Leu Arg Ile Gly Gln
            740                 745                 750

Lys Leu Ala Ile Met Gly Ala Thr Leu Asp Ala His Gly Glu Gly Lys
            755                 760                 765

Glu Val Leu Ser Ala Tyr Arg Met Ser Asn Leu Val Leu Thr Ala Asn
            770                 775                 780

Ser Val Ser Leu Ala Pro Trp Asp Ala Lys Leu Gly Phe Ala Ser Thr
785                 790                 795                 800

Pro Phe Cys Ala Ser Leu Arg Ser Leu Thr Pro Glu Gly Gly Leu Ile
            805                 810                 815

Ser Leu Met Asp Val Val Ile Thr Lys Val Tyr Pro Leu Ala Tyr Val
            820                 825                 830

Asp Val Asp Lys Ser Asn Ala Gly Ala Pro Arg Gly Glu Gln Glu Glu
            835                 840                 845

Ala Glu Gln Arg Glu Ala Trp Leu Gln Arg Arg Glu Asp Ala Met Leu
850                 855                 860

Gln Leu Glu Leu Glu Ala Glu Ala Glu Leu Gly Arg Leu Tyr Asp Leu
865                 870                 875                 880

Val Glu Ala Leu Asn Asp Leu Val Gly Asp Ala Phe Leu Pro Ser Ile
            885                 890                 895

Pro Asp Asp Pro Thr Gly Arg Leu Glu Ala Phe Ala Asn Gln Leu Phe
            900                 905                 910

Asp Gln Leu Arg Ala Gln Pro Asn Pro Ala Ser Ala Val Lys Glu Arg
            915                 920                 925

Val Val Thr Ala Gly His Thr Ser Leu Val Pro Trp Leu His Asn Leu
            930                 935                 940

Ala Lys Ser Ala Leu Leu Gln Glu Asp Gly Ile Arg Gly Ser Ser Leu
945                 950                 955                 960

Ser Ala Glu Leu Asp Arg Leu Cys Pro Pro Arg Lys Val Arg Glu Phe
            965                 970                 975

Arg Val Val Lys Phe Arg Asp Ala Arg Leu Pro Pro Gln Pro Pro Ala
            980                 985                 990

Thr Cys Leu Ser Thr Lys Thr Gln Gln Val Gly Gly Ser Gly Ala Thr
            995                 1000                1005

Ser Lys Arg Lys Asn Ala Tyr Ala Arg Ala Val Gln Leu Thr Val
            1010                1015                1020

Arg Asp Ala Ala Gln Leu Gly Asp Glu Leu Arg Glu Gly Arg Arg
            1025                1030                1035

Phe Leu Val Thr Asn Leu Val Pro Met Ser Lys Ser Ala Trp Arg
            1040                1045                1050
```

Lys Pro Asp Asp Gln Ala Glu Val Phe Leu Ser Thr Arg Arg Asp
    1055                1060                1065

Thr Lys Trp Arg Pro Val Ala
    1070            1075

<210> SEQ ID NO 30
<211> LENGTH: 432
<212> TYPE: PRT
<213> ORGANISM: Artificial Sequence
<220> FEATURE:
<223> OTHER INFORMATION: Synthetic Construct

<400> SEQUENCE: 30

Met Asp Thr Ile His His His His His His Asn Thr Ser Met Lys Ile
1               5                   10                  15

Glu Glu Gly Lys Leu Val Ile Trp Ile Asn Gly Asp Lys Gly Tyr Asn
                20                  25                  30

Gly Leu Ala Glu Val Gly Lys Lys Phe Glu Lys Asp Thr Gly Ile Lys
            35                  40                  45

Val Thr Val Glu His Pro Asp Lys Leu Glu Glu Lys Phe Pro Gln Val
    50                  55                  60

Ala Ala Thr Gly Asp Gly Pro Asp Ile Ile Phe Trp Ala His Asp Arg
65                  70                  75                  80

Phe Gly Gly Tyr Ala Gln Ser Gly Leu Leu Ala Glu Ile Thr Pro Asp
                85                  90                  95

Lys Ala Phe Gln Asp Lys Leu Tyr Pro Phe Thr Trp Asp Ala Val Arg
            100                 105                 110

Tyr Asn Gly Lys Leu Ile Ala Tyr Pro Ile Ala Val Glu Ala Leu Ser
        115                 120                 125

Leu Ile Tyr Asn Lys Asp Leu Leu Pro Asn Pro Pro Lys Thr Trp Glu
    130                 135                 140

Glu Ile Pro Ala Leu Asp Lys Glu Leu Lys Ala Lys Gly Lys Ser Ala
145                 150                 155                 160

Leu Met Phe Asn Leu Gln Glu Pro Tyr Phe Thr Trp Pro Leu Ile Ala
                165                 170                 175

Ala Asp Gly Gly Tyr Ala Phe Lys Tyr Glu Asn Gly Lys Tyr Asp Ile
            180                 185                 190

Lys Asp Val Gly Val Asp Asn Ala Gly Ala Lys Ala Gly Leu Thr Phe
        195                 200                 205

Leu Val Asp Leu Ile Lys Asn Lys His Met Asn Ala Asp Thr Asp Tyr
    210                 215                 220

Ser Ile Ala Glu Ala Ala Phe Asn Lys Gly Glu Thr Ala Met Thr Ile
225                 230                 235                 240

Asn Gly Pro Trp Ala Trp Ser Asn Ile Asp Thr Ser Lys Val Asn Tyr
                245                 250                 255

Gly Val Thr Val Leu Pro Thr Phe Lys Gly Gln Pro Ser Lys Pro Phe
            260                 265                 270

Val Gly Val Leu Ser Ala Gly Ile Asp Ala Ala Ser Pro Asn Lys Glu
        275                 280                 285

Leu Ala Lys Glu Phe Leu Glu Asn Tyr Leu Leu Thr Asp Glu Gly Leu
    290                 295                 300

Glu Ala Val Asn Lys Asp Lys Pro Leu Gly Ala Val Ala Leu Lys Ser
305                 310                 315                 320

Tyr Glu Glu Glu Leu Ala Lys Asp Pro Arg Ile Ala Ala Thr Met Glu
                325                 330                 335

```
Asn Ala Gln Lys Gly Glu Ile Met Pro Asn Ile Pro Gln Met Ser Ala
            340                 345                 350

Phe Trp Tyr Ala Val Arg Thr Ala Val Ile Asn Ala Ala Ser Gly Arg
        355                 360                 365

Gln Thr Val Asp Glu Ala Leu Lys Asp Ala Gln Thr Asn Ser Ser Ser
    370                 375                 380

Thr Ser Gly Ser Gly Gly Ala Arg Leu Glu Asn Leu Tyr Phe Gln Gly
385                 390                 395                 400

Ser Lys Glu Pro Thr Leu Leu Gly Phe His Thr Gly Ser Gly Lys Lys
                405                 410                 415

Val Lys Ile Ala Lys Glu Ser Leu Asp Lys Val Lys Asn Leu Phe Asp
            420                 425                 430

<210> SEQ ID NO 31
<211> LENGTH: 432
<212> TYPE: PRT
<213> ORGANISM: Artificial Sequence
<220> FEATURE:
<223> OTHER INFORMATION: Synthetic Construct

<400> SEQUENCE: 31

Met Asp Thr Ile His His His His His Asn Thr Ser Met Lys Ile
1               5                   10                  15

Glu Glu Gly Lys Leu Val Ile Trp Ile Asn Gly Asp Lys Gly Tyr Asn
            20                  25                  30

Gly Leu Ala Glu Val Gly Lys Lys Phe Glu Lys Asp Thr Gly Ile Lys
        35                  40                  45

Val Thr Val Glu His Pro Asp Lys Leu Glu Glu Lys Phe Pro Gln Val
    50                  55                  60

Ala Ala Thr Gly Asp Gly Pro Asp Ile Ile Phe Trp Ala His Asp Arg
65                  70                  75                  80

Phe Gly Gly Tyr Ala Gln Ser Gly Leu Leu Ala Glu Ile Thr Pro Asp
                85                  90                  95

Lys Ala Phe Gln Asp Lys Leu Tyr Pro Phe Thr Trp Asp Ala Val Arg
            100                 105                 110

Tyr Asn Gly Lys Leu Ile Ala Tyr Pro Ile Ala Val Glu Ala Leu Ser
        115                 120                 125

Leu Ile Tyr Asn Lys Asp Leu Leu Pro Asn Pro Pro Lys Thr Trp Glu
130                 135                 140

Glu Ile Pro Ala Leu Asp Lys Glu Leu Lys Ala Lys Gly Lys Ser Ala
145                 150                 155                 160

Leu Met Phe Asn Leu Gln Glu Pro Tyr Phe Thr Trp Pro Leu Ile Ala
                165                 170                 175

Ala Asp Gly Gly Tyr Ala Phe Lys Tyr Glu Asn Gly Lys Tyr Asp Ile
            180                 185                 190

Lys Asp Val Gly Val Asp Asn Ala Gly Ala Lys Ala Gly Leu Thr Phe
        195                 200                 205

Leu Val Asp Leu Ile Lys Asn Lys His Met Asn Ala Asp Thr Asp Tyr
210                 215                 220

Ser Ile Ala Glu Ala Ala Phe Asn Lys Gly Glu Thr Ala Met Thr Ile
225                 230                 235                 240

Asn Gly Pro Trp Ala Trp Ser Asn Ile Asp Thr Ser Lys Val Asn Tyr
                245                 250                 255

Gly Val Thr Val Leu Pro Thr Phe Lys Gly Gln Pro Ser Lys Pro Phe
            260                 265                 270
```

-continued

```
Val Gly Val Leu Ser Ala Gly Ile Asp Ala Ala Ser Pro Asn Lys Glu
            275                 280                 285

Leu Ala Lys Glu Phe Leu Glu Asn Tyr Leu Leu Thr Asp Gly Leu
    290                 295                 300

Glu Ala Val Asn Lys Asp Lys Pro Leu Gly Ala Val Ala Leu Lys Ser
305                 310                 315                 320

Tyr Glu Glu Leu Ala Lys Asp Pro Arg Ile Ala Ala Thr Met Glu
            325                 330                 335

Asn Ala Gln Lys Gly Glu Ile Met Pro Asn Ile Pro Gln Met Ser Ala
            340                 345                 350

Phe Trp Tyr Ala Val Arg Thr Ala Val Ile Asn Ala Ala Ser Gly Arg
            355                 360                 365

Gln Thr Val Asp Glu Ala Leu Lys Asp Ala Gln Thr Asn Ser Ser Ser
    370                 375                 380

Thr Ser Gly Ser Gly Gly Ala Arg Leu Glu Asn Leu Tyr Phe Gln Gly
385                 390                 395                 400

Ser Lys Glu Pro Thr Leu Leu Gly Trp His Thr Gly Ser Gly Lys Lys
            405                 410                 415

Val Lys Ile Ala Lys Glu Ser Leu Asp Lys Val Lys Asn Leu Phe Asp
            420                 425                 430
```

<210> SEQ ID NO 32
<211> LENGTH: 432
<212> TYPE: PRT
<213> ORGANISM: Artificial Sequence
<220> FEATURE:
<223> OTHER INFORMATION: Synthetic Construct

<400> SEQUENCE: 32

```
Met Asp Thr Ile His His His His His Asn Thr Ser Met Lys Ile
1               5                   10                  15

Glu Glu Gly Lys Leu Val Ile Trp Ile Asn Gly Asp Lys Gly Tyr Asn
            20                  25                  30

Gly Leu Ala Glu Val Gly Lys Lys Phe Glu Lys Asp Thr Gly Ile Lys
        35                  40                  45

Val Thr Val Glu His Pro Asp Lys Leu Glu Glu Lys Phe Pro Gln Val
    50                  55                  60

Ala Ala Thr Gly Asp Gly Pro Asp Ile Ile Phe Trp Ala His Asp Arg
65                  70                  75                  80

Phe Gly Gly Tyr Ala Gln Ser Gly Leu Leu Ala Glu Ile Thr Pro Asp
                85                  90                  95

Lys Ala Phe Gln Asp Lys Leu Tyr Pro Phe Thr Trp Asp Ala Val Arg
            100                 105                 110

Tyr Asn Gly Lys Leu Ile Ala Tyr Pro Ile Ala Val Glu Ala Leu Ser
        115                 120                 125

Leu Ile Tyr Asn Lys Asp Leu Leu Pro Asn Pro Pro Lys Thr Trp Glu
    130                 135                 140

Glu Ile Pro Ala Leu Asp Lys Glu Leu Lys Ala Lys Gly Lys Ser Ala
145                 150                 155                 160

Leu Met Phe Asn Leu Gln Glu Pro Tyr Phe Thr Trp Pro Leu Ile Ala
                165                 170                 175

Ala Asp Gly Gly Tyr Ala Phe Lys Tyr Glu Asn Gly Lys Tyr Asp Ile
            180                 185                 190

Lys Asp Val Gly Val Asp Asn Ala Gly Ala Lys Ala Gly Leu Thr Phe
        195                 200                 205
```

-continued

```
Leu Val Asp Leu Ile Lys Asn Lys His Met Asn Ala Asp Thr Asp Tyr
    210                 215                 220
Ser Ile Ala Glu Ala Ala Phe Asn Lys Gly Glu Thr Ala Met Thr Ile
225                 230                 235                 240
Asn Gly Pro Trp Ala Trp Ser Asn Ile Asp Thr Ser Lys Val Asn Tyr
            245                 250                 255
Gly Val Thr Val Leu Pro Thr Phe Lys Gly Gln Pro Ser Lys Pro Phe
            260                 265                 270
Val Gly Val Leu Ser Ala Gly Ile Asp Ala Ala Ser Pro Asn Lys Glu
        275                 280                 285
Leu Ala Lys Glu Phe Leu Glu Asn Tyr Leu Leu Thr Asp Glu Gly Leu
    290                 295                 300
Glu Ala Val Asn Lys Asp Lys Pro Leu Gly Ala Val Ala Leu Lys Ser
305                 310                 315                 320
Tyr Glu Glu Glu Leu Ala Lys Asp Pro Arg Ile Ala Ala Thr Met Glu
            325                 330                 335
Asn Ala Gln Lys Gly Glu Ile Met Pro Asn Ile Pro Gln Met Ser Ala
            340                 345                 350
Phe Trp Tyr Ala Val Arg Thr Ala Val Ile Asn Ala Ala Ser Gly Arg
            355                 360                 365
Gln Thr Val Asp Glu Ala Leu Lys Asp Ala Gln Thr Asn Ser Ser Ser
    370                 375                 380
Thr Ser Gly Ser Gly Gly Ala Arg Leu Glu Asn Leu Tyr Phe Gln Gly
385                 390                 395                 400
Ser Lys Glu Pro Thr Leu Leu Gly Trp His Thr Ser Ser Gly Lys Lys
            405                 410                 415
Val Lys Ile Ala Lys Glu Ser Leu Asp Lys Val Lys Asn Leu Phe Asp
            420                 425                 430
```